United States Patent
Inoue et al.

(10) Patent No.: US 10,288,412 B2
(45) Date of Patent: May 14, 2019

(54) OPTICAL MEASUREMENT APPARATUS AND OPTICAL MEASUREMENT METHOD

(71) Applicant: Otsuka Electronics Co., Ltd., Osaka (JP)

(72) Inventors: Nobuyuki Inoue, Kyoto (JP); Kunikazu Taguchi, Hirakata (JP)

(73) Assignee: Otsuka Electronics Co., Ltd., Osaka (JP)

( * ) Notice: Subject to any disclaimer, the term of this patent is extended or adjusted under 35 U.S.C. 154(b) by 0 days.

(21) Appl. No.: 15/996,941

(22) Filed: Jun. 4, 2018

(65) Prior Publication Data

US 2018/0347964 A1 Dec. 6, 2018

(30) Foreign Application Priority Data

Jun. 5, 2017 (JP) .................. 2017-111043

(51) Int. Cl.
*G01B 11/06* (2006.01)
*G01B 9/02* (2006.01)

(52) U.S. Cl.
CPC .......... *G01B 11/06* (2013.01); *G01B 9/02024* (2013.01); *G01B 9/02041* (2013.01); *G01B 9/02043* (2013.01)

(58) Field of Classification Search
CPC ...... G01B 11/06; G01B 9/06; G01B 9/02024; G01B 9/02041; G01B 9/02043
(Continued)

(56) References Cited

U.S. PATENT DOCUMENTS

| 5,034,617 A | 7/1991 | Isobe |
| 2011/0102812 A1 | 5/2011 | Nishida |

(Continued)

FOREIGN PATENT DOCUMENTS

| JP | H06-034525 A | 2/1994 |
| JP | 2000-275016 A | 10/2000 |

(Continued)

OTHER PUBLICATIONS

An Office Action; "Decision to Grant Patent," mailed by the Japanese Patent Office dated Jan. 23, 2018, which corresponds to Japanese Patent Application No. 2017-111043.

(Continued)

*Primary Examiner* — Hina F Ayub
(74) *Attorney, Agent, or Firm* — Studebaker & Brackett PC

(57) ABSTRACT

An optical measurement apparatus includes an irradiation optical system which linearly irradiates a measurement target with measurement light having a certain wavelength range, a measurement optical system which receives linear measurement interference light which is transmitted light or reflected light originating from the measurement target as a result of irradiation with the measurement light, and a processing device. The processing device includes a first calculation module that calculates a modification factor depending on with an angle of incidence on the measurement optical system from each measurement point in association with a region in the two-dimensional image corresponding to each measurement point in the measurement target irradiated with the measurement light and a second calculation module that calculates optical characteristics of the measurement target by applying the corresponding modification factor to a value for each pixel included in the two-dimensional image.

10 Claims, 27 Drawing Sheets

(58) Field of Classification Search
USPC .......................................................... 356/503
See application file for complete search history.

(56) References Cited

U.S. PATENT DOCUMENTS

| | | | |
|---|---|---|---|
| 2011/0194113 A1* | 8/2011 | Sakai | G01B 11/06 |
| | | | 356/432 |
| 2014/0185060 A1 | 7/2014 | Doerband et al. | |
| 2015/0022810 A1* | 1/2015 | Kobayashi | G01J 3/502 |
| | | | 356/319 |

FOREIGN PATENT DOCUMENTS

| | | | |
|---|---|---|---|
| JP | 2004-279296 A | 10/2004 | |
| JP | 2009-092454 A | 4/2009 | |
| JP | 2011-095138 A | 5/2011 | |
| JP | 2011-196766 A | 10/2011 | |
| JP | 2012-122768 A | 6/2012 | |
| JP | 2012-189406 A | 10/2012 | |
| JP | 2013-044729 A | 3/2013 | |
| JP | 2013-079921 A | 5/2013 | |
| JP | 2015-017804 A | 1/2015 | |

OTHER PUBLICATIONS

Decision to Grant Patent mailed by the Japanese Patent Office dated Jul. 3, 2018, which corresponds to Japanese Patent Application No. 2018-012204 and is related to U.S. Appl. No. 15/996,941.

A Notice of Allowance mailed by the U.S. Patent and Trademark Office dated Feb. 8, 2019, which corresponds to U.S. Appl. No. 15/996,970 and is related to U.S. Appl. No. 15/996,941.

\* cited by examiner

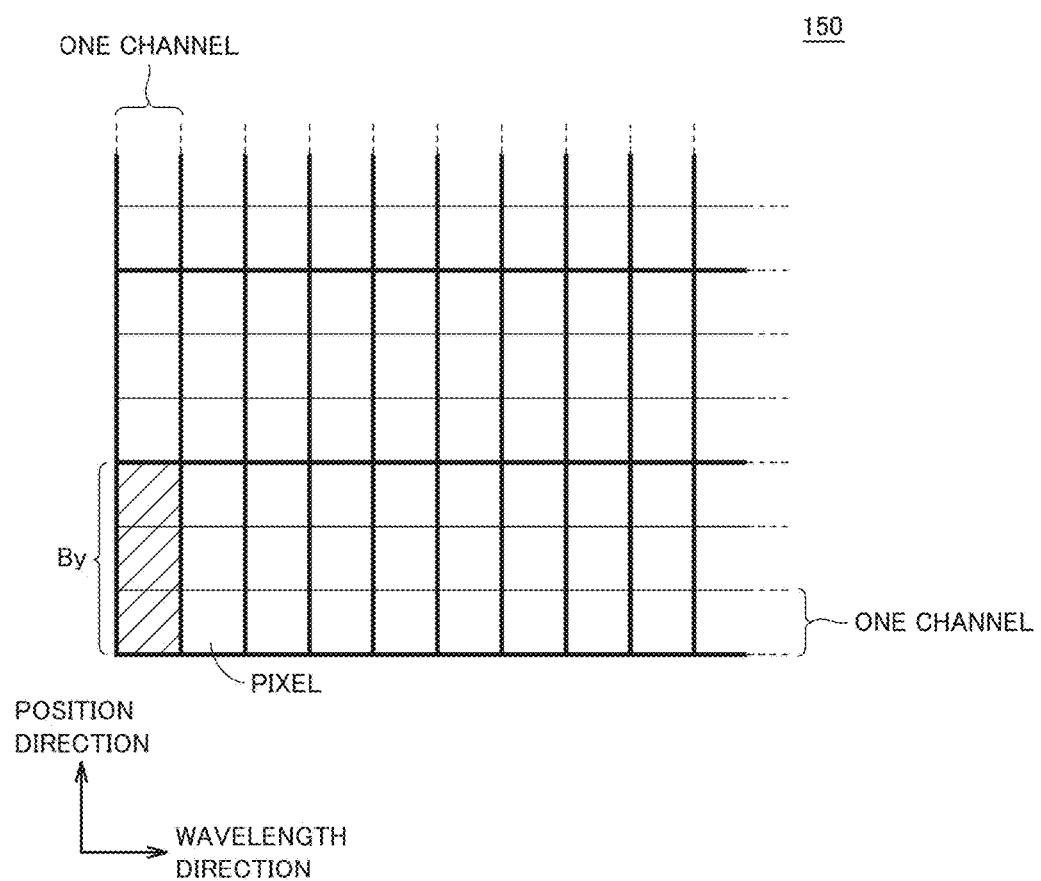

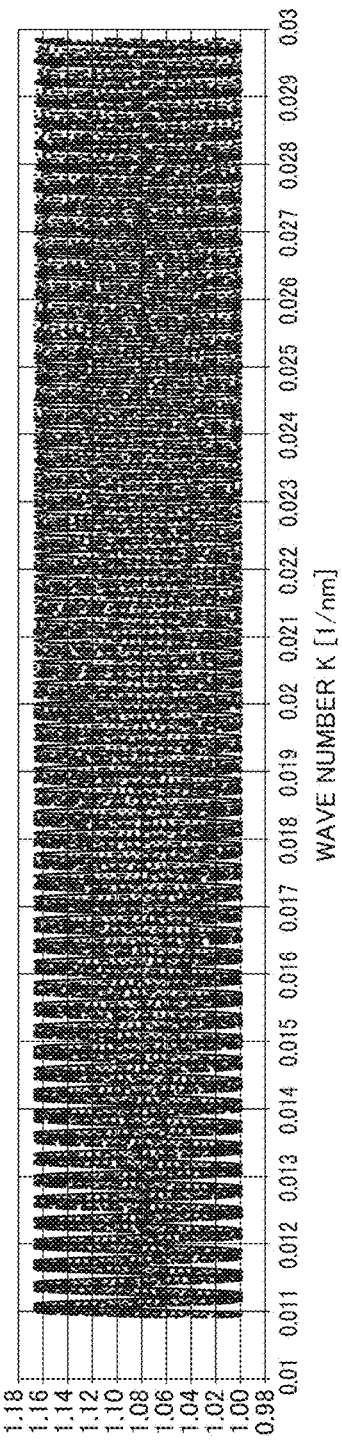
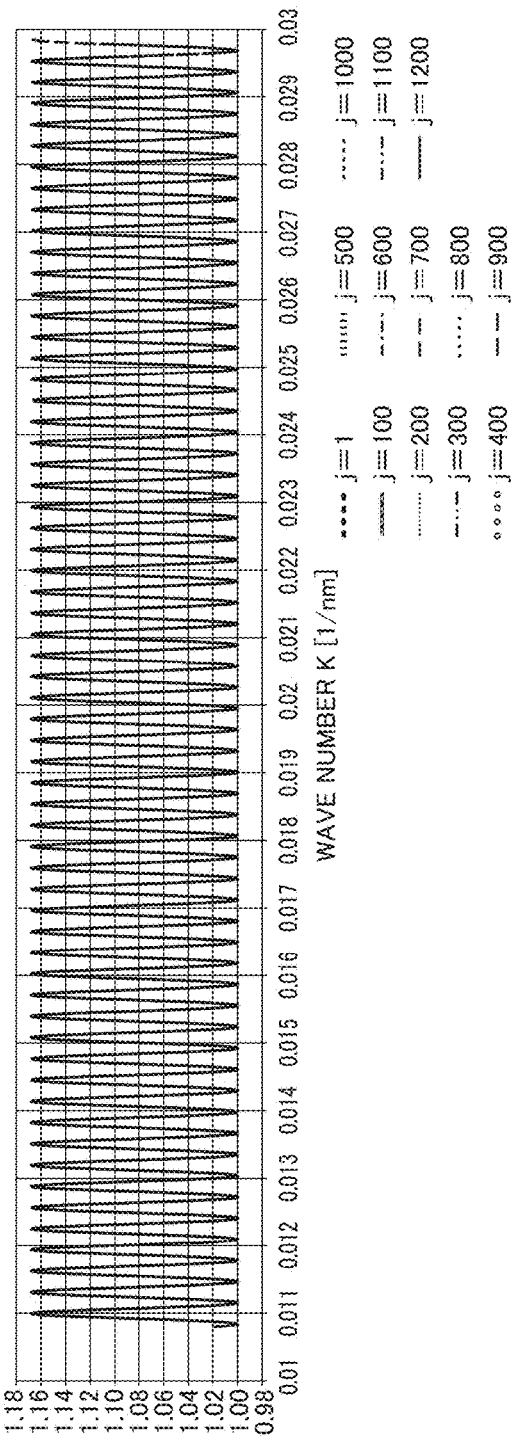
FIG.17A
FIG.17B

OPTICAL MEASUREMENT APPARATUS AND OPTICAL MEASUREMENT METHOD

BACKGROUND OF THE INVENTION

Field of the Invention

The present technical concept relates to an optical measurement apparatus and an optical measurement method capable of measuring optical characteristics such as a film thickness and a refractive index.

Description of the Background Art

A technique to measure a film thickness of a sample such as a functional resin film or a semiconductor substrate has been known. For example, Japanese Patent Laying-Open No. 2009-092454 discloses a multi-layered film analysis apparatus and a multi-layered film analysis method capable of highly accurately measuring a film thickness of a multi-layered film sample having wavelength-dependency. Japanese Patent Laying-Open No. 2013-079921 discloses a film thickness measurement apparatus and a film thickness measurement method capable of accurately measuring a thickness of a dielectric thin film of which refractive index is not known.

In general, a sample to be subjected to measurement has a certain area, and there is a need for quick measurement of a film thickness distribution (an in-plane film thickness distribution) at a surface to be subjected to measurement. In order to meet such needs, Japanese Patent Laying-Open No. 2004-279296 discloses an approach for quickly obtaining a thickness distribution of a formed thin film with a simplified apparatus configuration in forming a thin film on a flat plate in a process for manufacturing a liquid crystal display. More specifically, Japanese Patent Laying-Open No. 2004-279296 discloses a method of allowing light emitted from a light source to enter a coating provided on a substrate to be subjected to measurement, measuring light reflected from the coating which has caused interference with a light reception apparatus with an angle of incidence of the light emitted to a main surface of the coating being varied stepwise, and obtaining a thickness of the coating based on the angle of incidence of the emitted light which takes a relative maximum value and a relative minimum value in variation in intensity of reception of measured reflected light.

With increase in size of a sample, there is a need for measurement of an in-plane film thickness distribution of a larger sample at a higher speed and with higher accuracy. The configurations disclosed in Japanese Patent Laying-Open No. 2009-092454 and Japanese Patent Laying-Open No. 2013-079921 are basically directed to measurement by irradiation with light to one certain point of a sample, and they are unable to sufficiently meet the need for quick measurement of an in-plane film thickness distribution.

Japanese Patent Laying-Open No. 2004-279296 adopts what is called a peak-valley method of calculating a film thickness by using positions where a relative maximum value and a relative minimum value of an interference waveform are produced. With the peak-valley method, a film thickness may not accurately be measured under the influence by noise originating from an optical system. In addition, with the peak-valley method, a thickness of each layer of a sample in which a plurality of layers are stacked cannot be measured. Therefore, though Japanese Patent Laying-Open No. 2004-279296 may be applicable to a process for manufacturing a liquid crystal display, it is unable to measure an in-plane film thickness distribution of various samples in general.

SUMMARY OF THE INVENTION

One object of the present technical concept is to provide an optical measurement apparatus and an optical measurement method capable of measuring an in-plane film thickness distribution of various samples at a higher speed and with higher accuracy. Another object of the present technical concept is to provide an optical measurement apparatus and an optical measurement method capable of measuring optical characteristics of a sample such as a refractive index without using a dedicated measurement apparatus.

An optical measurement apparatus according to one embodiment includes an irradiation optical system configured to linearly irradiate a measurement target with measurement light having a certain wavelength range, a measurement optical system which receives linear measurement interference light which is transmitted light or reflected light originating from the measurement target as a result of irradiation with the measurement light, and a processing device. The measurement optical system includes a diffraction grating which expands the measurement interference light in a wavelength direction orthogonal to a longitudinal direction of the measurement interference light and an imaging portion which outputs a two-dimensional image by receiving the measurement interference light expanded in the wavelength direction by the diffraction grating. The processing device includes a first calculation module that calculates a modification factor depending on an angle of incidence on the measurement optical system from each measurement point in association with a region in the two-dimensional image corresponding to each measurement point in the measurement target irradiated with the measurement light and a second calculation module that calculates optical characteristics of the measurement target by applying a corresponding modification factor to each pixel value included in the two-dimensional image.

The modification factor may include a wave number representing a parameter including a wavelength of the measurement light and a refractive index of the measurement target. The wave number is calculated in consideration of magnitude of a corresponding angle of incidence, for each pixel position in the two-dimensional image.

The second calculation module may subject a row of values resulting from conversion in accordance with a relational expression for linearizing the pixel value of the two-dimensional image corresponding to a measurement point of interest with respect to a phase factor, to Fourier transform with respect to a row of corresponding wave numbers, determine a film thickness at the measurement point of interest based on a peak position which appears in a power spectrum obtained through Fourier transform, and aggregate film thicknesses determined for a plurality of measurement points and outputting the resultant aggregate as a film thickness distribution.

The wave number may be calculated in consideration of wavelength-dependency of a refractive index of the measurement target.

The modification factor may include a value representing magnitude of an angle of incidence corresponding to each measurement point. The second calculation module may adopt a film thickness at each measurement point as a fluctuating parameter and calculate a theoretical value of each pixel corresponding to the two-dimensional image based on a refractive index of the measurement target, a value representing magnitude of the angle of incidence corresponding to each measurement point, and correspondence between each measurement point and a pixel position in the two-dimensional image and determine a film thickness at each measurement point by adjusting the fluctuating parameter such that a similarity between the calculated theoretical value of each pixel and each pixel value of the two-dimensional image is higher.

An optical measurement method according to another embodiment includes linearly irradiating a measurement target with measurement light having a certain wavelength range and receiving linear measurement interference light which is transmitted light or reflected light originating from the measurement target as a result of irradiation with the measurement light, expanding the measurement interference light in a wavelength direction orthogonal to a longitudinal direction of the measurement interference light and outputting a two-dimensional image by receiving the measurement interference light expanded in the wavelength direction, calculating a modification factor depending on an angle of incidence from each measurement point in association with a region in the two-dimensional image corresponding to each measurement point in the measurement target irradiated with the measurement light, and calculating optical characteristics of the measurement target by applying a corresponding modification factor to each pixel value included in the two-dimensional image.

The modification factor may include a wave number representing a parameter including a wavelength of the measurement light and a refractive index of the measurement target. The wave number may be calculated in consideration of magnitude of a corresponding angle of incidence, for each pixel position in the two-dimensional image.

The calculating optical characteristics may include subjecting a row of values resulting from conversion in accordance with a relational expression for linearizing the pixel value of the two-dimensional image corresponding to a measurement point of interest with respect to a phase factor, to Fourier transform with respect to a row of corresponding wave numbers, determining a film thickness at the measurement point of interest based on a peak position which appears in a power spectrum obtained through Fourier transform, and aggregating film thicknesses determined for a plurality of measurement points and outputting the resultant aggregate as a film thickness distribution.

The wave number may be calculated in consideration of wavelength-dependency of a refractive index of the measurement target.

The modification factor may include a value representing magnitude of an angle of incidence corresponding to each measurement point. The calculating optical characteristics may include adopting a film thickness at each measurement point as a fluctuating parameter and calculating a theoretical value of each pixel corresponding to the two-dimensional image based on a refractive index of the measurement target, a value representing magnitude of the angle of incidence corresponding to each measurement point, and correspondence between each measurement point and a pixel position in the two-dimensional image and determine a film thickness at each measurement point by adjusting the fluctuating parameter such that a similarity between the calculated theoretical value of each pixel and each pixel value of the two-dimensional image is higher.

According to yet another embodiment, an optical measurement method with an optical measurement apparatus including an irradiation optical system and a measurement optical system is provided, the irradiation optical system being configured to linearly irradiate a measurement target with measurement light having a certain wavelength range, the measurement optical system being configured to output a two-dimensional image by expanding linear measurement interference light in a wavelength direction orthogonal to a longitudinal direction of the measurement interference light, the measurement interference light being transmitted light or reflected light originating from the measurement target as a result of irradiation with the measurement light. The optical measurement method includes obtaining a distribution of actually measured values when angles of incidence are different for the same sample, calculating a modification factor depending on an angle of incidence on the measurement optical system from each measurement point in association with a region in the two-dimensional image corresponding to each measurement point in the measurement target irradiated with the measurement light, and calculating optical characteristics including a refractive index of the sample based on a group of pixel values in one row or a plurality of rows along any one direction in the distribution of the actually measured values and corresponding modification factors.

The calculating optical characteristics may include calculating film thicknesses at a plurality of positions in the distribution of the actually measured values based on a set refractive index, a modification factor corresponding to each position, and a group of pixel values in a wavelength direction at each position, calculating a film thickness dispersion which is a dispersion for the calculated film thicknesses, repeating the calculating film thicknesses and the calculating a film thickness dispersion, with the refractive index of the sample being set to a plurality of different values, and determining a refractive index of the sample based on the calculated film thickness dispersion.

The determining a refractive index of the sample may include determining a refractive index at which the calculated film thickness dispersion becomes small as a refractive index of the sample.

The determining a refractive index of the sample may include fitting a polynomial representing a predetermined film thickness dispersion to relation between a refractive index and a film thickness dispersion and determining a refractive index of the sample based on a point at which the film thickness dispersion represented by the polynomial determined by fitting takes an extreme value.

The determining a refractive index of the sample may include fitting a polynomial representing a predetermined squared residual value to relation between a refractive index and a squared residual value for the calculated film thicknesses and determining a refractive index of the sample based on a point at which the squared residual value represented by the polynomial determined by fitting takes an extreme value.

A refractive index of the sample may be calculated in accordance with a prescribed wavelength dispersion formula. The determining a refractive index of the sample may include applying a least squares method to any of relation between each coefficient defining the wavelength dispersion formula and a film thickness dispersion and relation between each coefficient defining the wavelength dispersion formula and a squared residual value and determining a refractive index of the sample based on a set of coefficients at the time when the film thickness dispersion or the squared residual value takes an extreme value.

The calculating optical characteristics may include calculating a distribution of actually measured values exhibited by a group of pixel values in a position direction for any wavelength in the distribution of the actually measured values, calculating a distribution of theoretical values for any wavelength based on a film thickness and a refractive index of the sample that are set in advance and a modification factor corresponding to each position, and determining a film thickness and a refractive index of the sample so as to decrease an error between the distribution of the theoretical values and the distribution of the actually measured values.

The calculating optical characteristics may include determining a refractive index of the sample for each of a plurality of wavelengths in the distribution of the actually measured values.

The calculating optical characteristics may include calculating film thicknesses of the sample for a plurality of wavelengths in the distribution of the actually measured values based on the error between the distribution of the theoretical values and the distribution of the actually measured values and determining a more probable film thickness based on the calculated film thicknesses.

The refractive index of the sample used for calculation of the distribution of the theoretical values may be calculated in accordance with a prescribed wavelength dispersion formula. The calculating optical characteristics may include fitting each coefficient defining the prescribed wavelength dispersion formula and the film thickness so as to decrease errors between the distribution of the theoretical values and the distribution of the actually measured values for a plurality of wavelengths in the distribution of the actually measured values.

An optical measurement apparatus according to still another embodiment includes an irradiation optical system configured to linearly irradiate a measurement target with measurement light having a certain wavelength range, a measurement optical system configured to output a two-dimensional image by expanding linear measurement interference light in a wavelength direction orthogonal to a longitudinal direction of the measurement interference light, the measurement interference light being transmitted light or reflected light originating from the measurement target as a result of irradiation with the measurement light, and a processing device. The processing device may obtain a distribution of actually measured values when angles of incidence are different for the same sample, calculate a modification factor depending on an angle of incidence on the measurement optical system from each measurement point in association with a region in the two-dimensional image corresponding to each measurement point in the measurement target irradiated with the measurement light, and calculate optical characteristics including a refractive index of the sample based on a group of pixel values in one row or a plurality of rows along any one direction in the distribution of the actually measured values and corresponding modification factors.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 9 is a diagram for illustrating binning processing in calculating an angle of incidence used in the film thickness measurement method according to the present embodiment.

FIGS. 17A and 17B are graphs showing a wave-number-converted transmittance $T'(K_1)$ calculated from transmittance spectrum $T(\lambda)$ shown in FIG. 16.

DESCRIPTION OF THE PREFERRED EMBODIMENTS

Figure 1:
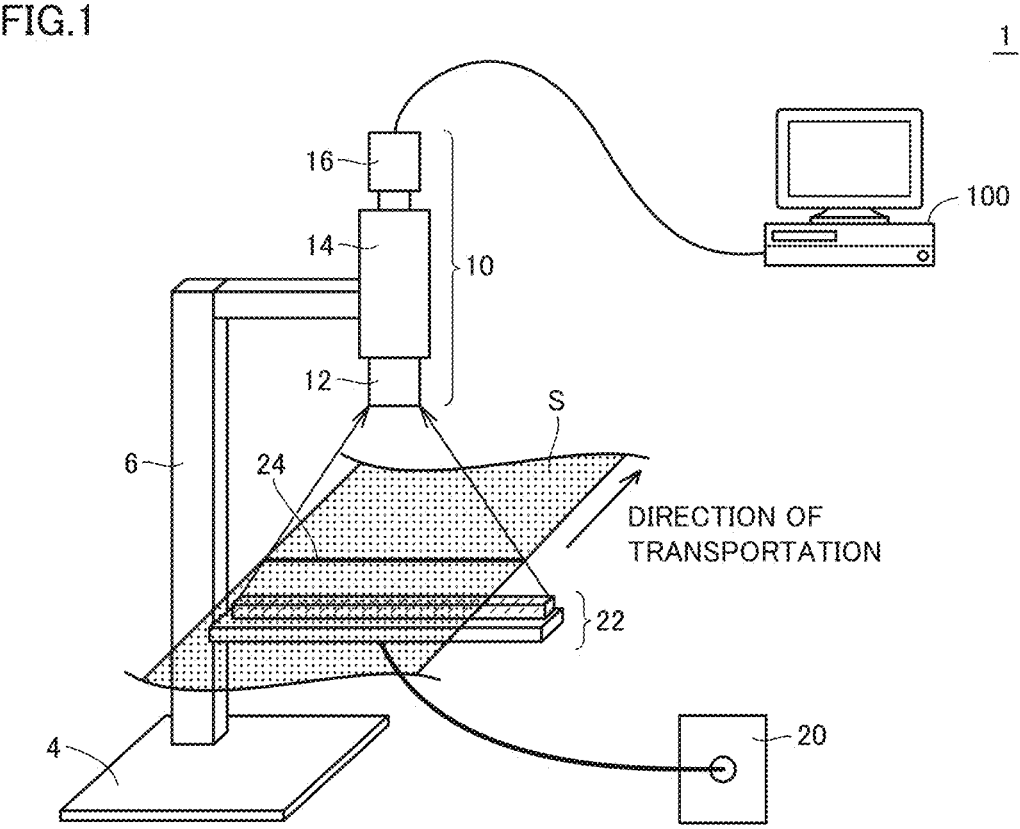
FIG. 1 is a schematic diagram showing a schematic configuration of a transmissive optical measurement apparatus according to the present embodiment.

An embodiment of the present invention will be described in detail with reference to the drawings. The same or corresponding elements in the drawings have the same reference characters allotted and description thereof will not be repeated.

A. Apparatus Configuration of Optical Measurement Apparatus

An apparatus configuration of an optical measurement apparatus according to the present embodiment will initially be described. The optical measurement apparatus according to the present embodiment is a measurement apparatus with an imaging spectroscope, and obtains wavelength information at each measurement point on a measurement line irradiated with measurement light by irradiating a measurement target (which is also referred to as a "sample" below) with linear measurement light and splitting light resulting from passage of the linear measurement light through the sample or reflected light resulting from reflection of the linear measurement light by the sample. Since transmitted light or reflected light originating from the sample exhibits results from occurrence of interference in the sample, it is also referred to as "measurement interference light" below.

A typical apparatus configuration of the optical measurement apparatus according to the present embodiment will be shown below.

(a1: Transmissive System)

FIG. 1 is a schematic diagram showing a schematic configuration of a transmissive optical measurement apparatus 1 according to the present embodiment. Referring to FIG. 1, optical measurement apparatus 1 includes a measurement optical system 10, a light source 20 configured to generate measurement light, a linear light guide 22 configured to irradiate a sample S with measurement light generated by light source 20, and a processing device 100.

Light source 20 and linear light guide 22 correspond to a linear light source unit (an irradiation optical system) which linearly irradiates sample S with light having a certain wavelength range. A wavelength range of the measurement light is determined by a range of wavelength information to be obtained from sample S. For example, a halogen lamp is employed as light source 20.

Linear light guide 22 is typically arranged directly under a surface where sample S is transported and irradiates sample S with measurement light from light source 20 through a linear opening. A diffusion member for suppressing unevenness in quantity of light is arranged on an irradiation surface of linear light guide 22. Measurement light from linear light guide 22 is incident on sample S, and a measurement line 24 irradiated with measurement light is produced.

Measurement optical system 10 receives linear measurement interference light which is transmitted light or reflected light originating from sample S as a result of irradiation with measurement light. More specifically, measurement optical system 10 obtains wavelength distribution characteristics of a transmittance or a reflectance at each measurement point based on measurement interference light which has passed through sample S or measurement interference light reflected by sample S. Measurement optical system 10 is arranged at a position opposed to linear light guide 22 with sample S lying therebetween. Light which has passed through sample S (measurement interference light) of measurement light irradiated from linear light guide 22 is incident on measurement optical system 10. Measurement optical system 10 is fixed by a base member 4 and a support member 6.

Measurement optical system 10 includes an object lens 12, an imaging spectroscope 14, and an imaging portion 16. Transmitted light from sample S is converged by object lens 12 and guided to imaging spectroscope 14.

Imaging spectroscope 14 collectively measures spectroscopic information at each measurement point on a line of sample S. More specifically, imaging spectroscope 14 expands incident linear transmitted light in a wavelength direction and outputs the expanded light to imaging portion 16. Imaging portion 16 is implemented by an imaging device having a two-dimensional light reception surface. Such an imaging device is implemented, for example, by a charge coupled device (CCD) image sensor or a complementary metal oxide semiconductor (CMOS) image sensor. Imaging portion 16 outputs a two-dimensional image by receiving transmitted light from imaging spectroscope 14 at the imaging device. The output two-dimensional image includes wavelength information and position information. Details of measurement optical system 10 will be described later.

Processing device 100 calculates a characteristic value of sample S such as a film thickness at each measurement point on measurement line 24 by performing processing as will be described later on the two-dimensional image output from measurement optical system 10 (imaging portion 16). Details of measurement processing by processing device 100 will be described later.

(a2: Reflective System)

Figure 2:
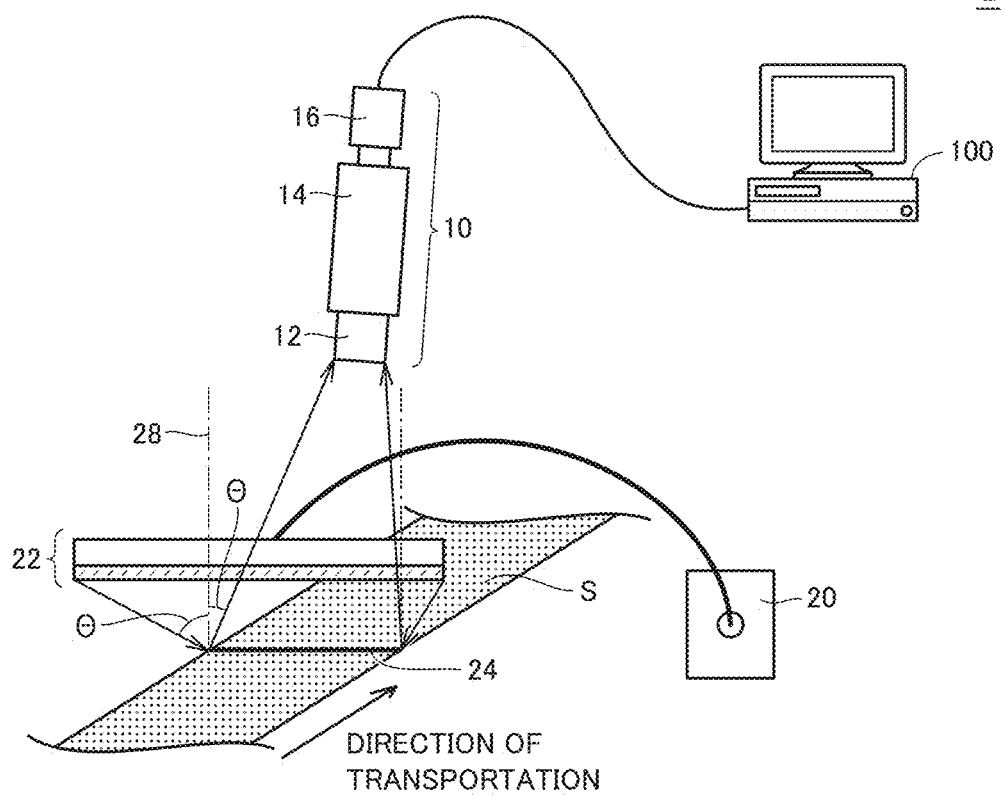
FIG. 2 is a schematic diagram showing a schematic configuration of a reflective optical measurement apparatus according to the present embodiment.

FIG. 2 is a schematic diagram showing a schematic configuration of a reflective optical measurement apparatus 2 according to the present embodiment. Referring to FIG. 2, optical measurement apparatus 2 is different from optical measurement apparatus 1 in positional relation of measurement optical system 10 and linear light guide 22. Specifically, linear light guide 22 is arranged such that measurement light to sample S forms an angle of incidence $\Theta$ (>0) with respect to a surface including measurement line 24 and a vertical direction 28. Measurement optical system 10 is arranged at a position where it can receive light resulting from reflection of measurement light incident on sample S (measurement interference light). Measurement optical system 10 is arranged such that an optical axis thereof forms the same angle of incidence Θ with respect to the surface including measurement line 24 and vertical direction 28.

Since optical measurement apparatus 2 is otherwise substantially the same in configuration as optical measurement apparatus 1, detailed description will not be repeated.

For the sake of convenience of description, details will be described basically with reference to optical measurement apparatus 1 which adopts the transmissive system.

(a3: Measurement Optical System)

Measurement optical system 10 adopted in the optical measurement apparatus according to the present embodiment will now be described.

Figure 3:
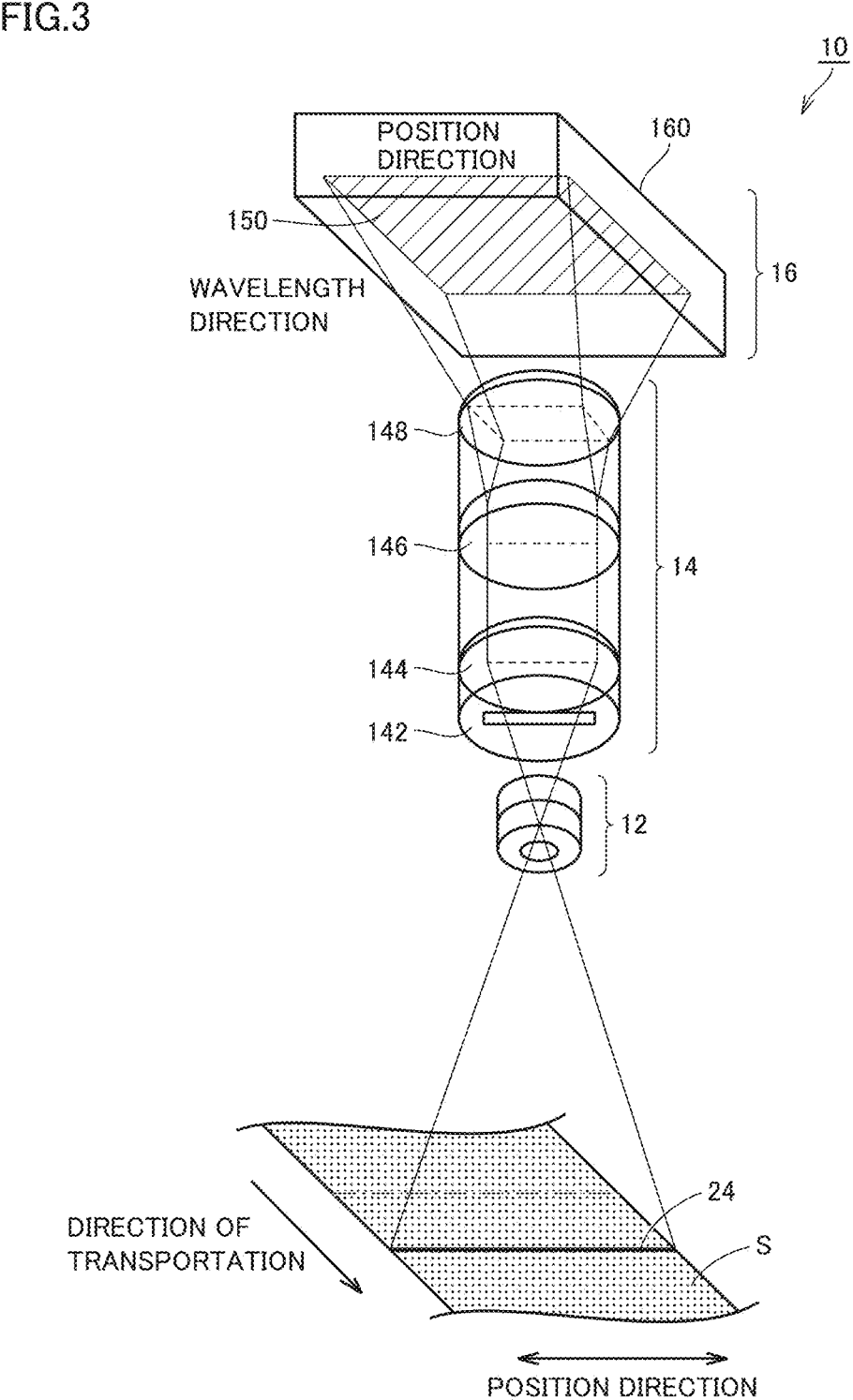
FIG. 3 is a schematic diagram showing a schematic configuration of a measurement optical system adopted in the optical measurement apparatus according to the present embodiment.

FIG. 3 is a schematic diagram showing a schematic configuration of measurement optical system 10 adopted in the optical measurement apparatus according to the present embodiment. Referring to FIG. 3, in measurement optical system 10, measurement interference light from sample S is incident on imaging spectroscope 14 after it forms an image on object lens 12.

Imaging spectroscope 14 includes a slit 142, a first lens 144, a diffraction grating 146, and a second lens 148 in the order of proximity to sample S.

Slit 142 shapes a cross-section of a beam of measurement interference light incident on object lens 12 into a prescribed shape. A length of slit 142 in a longitudinal direction is set to a length in accordance with measurement line 24 produced on sample S, and a width of slit 142 in a direction of a short side is set in accordance with a resolution of diffraction grating 146.

First lens 144 is typically implemented by a collimating lens, and it converts measurement interference light which has passed through slit 142 into parallel light and guides the parallel light to diffraction grating 146.

Diffraction grating 146 expands measurement interference light in a wavelength direction orthogonal to the longitudinal direction of measurement interference light. More specifically, diffraction grating 146 expands linear measurement interference light which has passed through object lens 12 and slit 142 in the wavelength direction orthogonal to a line direction. As a result of wavelength expansion by diffraction grating 146, a two-dimensional image 150 corresponding to the longitudinal direction of measurement line 24 and the direction orthogonal to the longitudinal direction is created on a light reception surface of an imaging device 160 of imaging portion 16. Imaging portion 16 outputs a two-dimensional image by receiving the measurement interference light which has been expanded by diffraction grating 146 in the wavelength direction. Though FIG. 3 shows an example in which a transmission diffraction grating is adopted as diffraction grating 146, a reflection diffraction grating may be adopted.

In the description below, a direction of two-dimensional image 150 corresponding to the longitudinal direction of measurement line 24 on sample S is referred to as a "position direction" and a direction of wavelength expansion orthogonal to the position direction is referred to as a "wavelength direction." Each point in the position direction corresponds to each measurement point on measurement line 24 and each point in the wavelength direction corresponds to each wavelength at a corresponding measurement point.

As shown in FIG. 3, measurement optical system 10 linearly takes in measurement interference light from sample S through object lens 12 and slit 142. Linear measurement interference light is converted to parallel light by first lens 144, and transmission or reflection diffraction grating 146 arranged in a stage subsequent to first lens 144 expands the linear measurement interference light in the direction orthogonal to the position direction (wavelength direction) (i.e., splits the linear measurement interference light). Second lens 148 arranged in a subsequent stage forms an image of the measurement interference light subjected to wavelength expansion as a two-dimensional optical spectrum which reflects wavelength information and position information. Two-dimensional imaging device 160 receives light of a formed image.

In the description below, the light reception surface of imaging device 160 has $C_x$ channels as a resolution in the wavelength direction and $C_y$ channels as a resolution in the position direction.

As described above, two-dimensional image 150 reflects wavelength information and position information. By using such a two-dimensional image 150, wavelength information at a plurality of measurement points set in sample S can collectively be obtained.

(a4: Position Adjustment Mechanism of Measurement Optical System)

A position adjustment mechanism of measurement optical system 10 which can be mounted on the optical measurement apparatus according to the present embodiment will now be described. In order to appropriately guide measurement interference light which has passed through sample S or measurement interference light reflected by sample S to measurement optical system 10, a position of measurement optical system 10 with respect to sample S should appropriately be adjusted. Some of such position adjustment mechanisms of measurement optical system 10 and position adjustment methods with the position adjustment mechanism will be described below.

Figure 4:
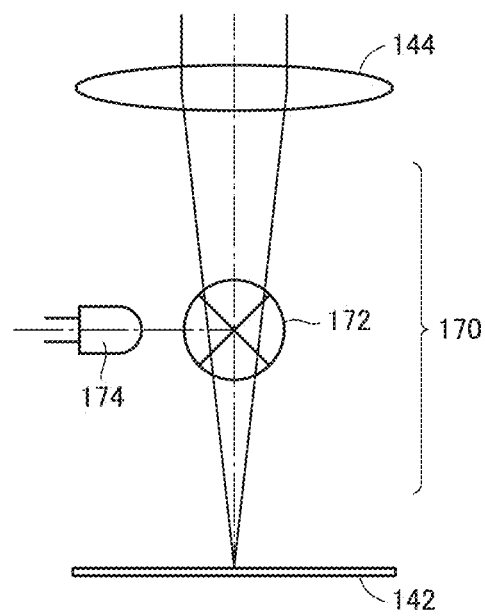
FIG. 4 is a schematic diagram showing a schematic configuration of a position adjustment mechanism adopted in the optical measurement apparatus according to the present embodiment.

FIG. 4 is a schematic diagram showing a schematic configuration of a position adjustment mechanism 170 adopted in the optical measurement apparatus according to the present embodiment. Position adjustment mechanism 170 shown in FIG. 4 is arranged between slit 142 and first lens 144. Position adjustment mechanism 170 includes a shutter 172 and a light source 174 which generates observation light. Observation light is light for adjustment of a position of a focus of measurement optical system 10 on sample S and adjustment of a position of observation of measurement optical system 10 with respect to sample S.

Shutter 172 is arranged at an intersection of an optical axis of slit 142 and first lens 144 and an optical axis of light source 174. Shutter 172 can make transition between an opened state and a closed state. In the opened state, shutter 172 allows passage of light from slit 142 toward first lens 144. In the closed state, shutter 172 cuts off an optical path from slit 142 toward first lens 144 and a mirror attached to a rear surface of shutter 172 reflects observation light from light source 174 toward slit 142. When shutter 172 is closed, sample S is irradiated with observation light from light source 174.

A user can appropriately adjust a distance (a position of a focus) from sample S to measurement optical system 10 by adjusting a position of measurement optical system 10 while the user views a state of observation light which appears on sample S, and can appropriately adjust a position on sample S observed by measurement optical system 10 (a position of a measurement site). By turning on light source 174, closing shutter 172, and adjusting a position of measurement optical system 10 or focus of object lens 12 so as to maximize a contrast of observation light which appears on sample S, a portion of measurement by measurement optical system 10 can be checked and focusing of measurement optical system 10 can be achieved.

In another method of adjusting a position of measurement optical system 10, a position of measurement optical system 10 may be adjusted by arranging a test chart instead of sample S and evaluating two-dimensional image 150 obtained by imaging the test chart with imaging portion 16. For example, a pattern such as the Ronchi ruling or monochrome stripes at regular intervals can be employed as the test chart. When such a pattern is used, a distance (a position of a focus) from sample S to measurement optical system 10 may be adjusted to maximize a ratio of contrast shown in actually imaged two-dimensional image 150.

B. Device Configuration of Processing Device

A device configuration of processing device 100 included in the optical measurement apparatus according to the present embodiment will now be described. Processing device 100 according to the present embodiment is typically implemented by a general-purpose computer.

Figure 5:
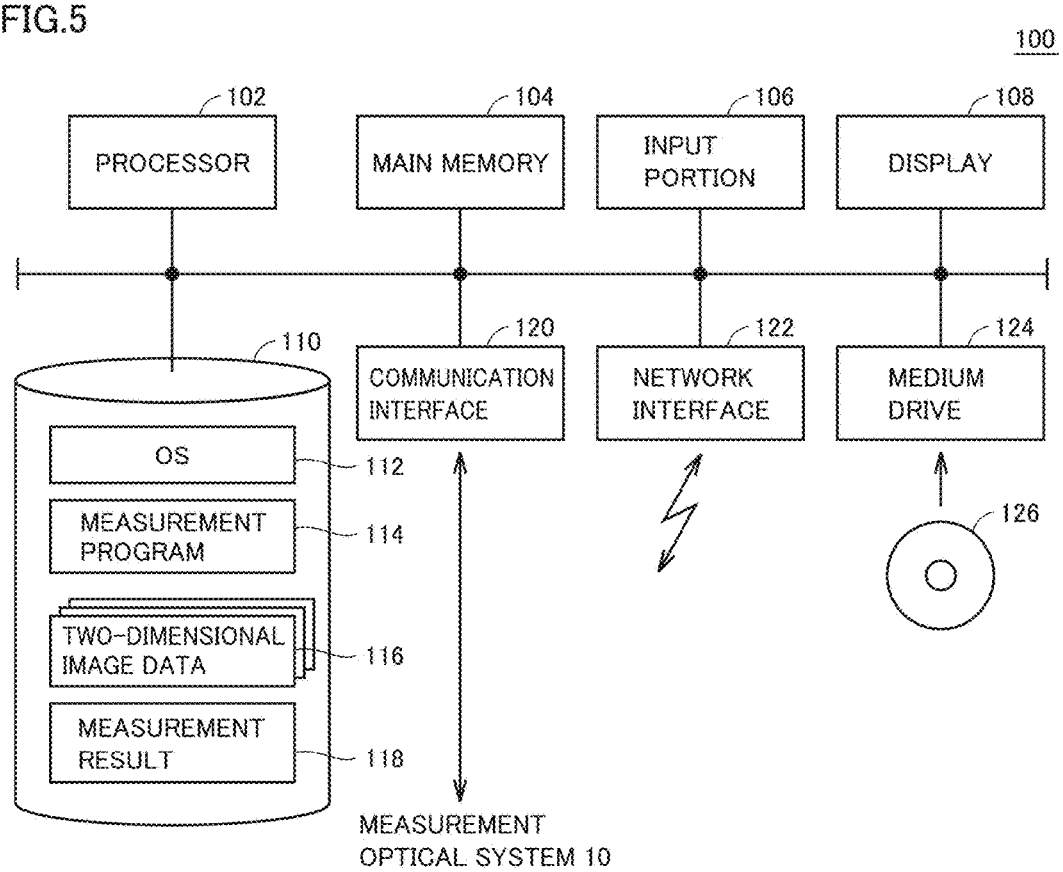
FIG. 5 is a schematic diagram showing a schematic configuration of a processing device according to the present embodiment.

FIG. 5 is a schematic diagram showing a schematic configuration of processing device 100 according to the present embodiment. Referring to FIG. 5, processing device 100 includes a processor 102, a main memory 104, an input portion 106, a display 108, a storage 110, a communication interface 120, a network interface 122, and a medium drive 124.

Processor 102 is typically an operational processing unit such as a central processing unit (CPU) and a graphics processing unit (GPU) and executes one program or a plurality of programs stored in storage 110 by reading the same into main memory 104.

Main memory 104 is a volatile memory such as a dynamic random access memory (DRAM) or a static random access memory (SRAM) and functions as a working memory for processor 102 to execute a program.

Input portion 106 includes a keyboard and/or a mouse and accepts an operation by a user. Display 108 outputs a result of execution of a program by processor 102 to the user.

Storage 110 is implemented by a non-volatile memory such as a hard disk or a flash memory and stores various programs and data. More specifically, storage 110 holds an operating system (OS) 112, a measurement program 114, two-dimensional image data 116, and a measurement result 118.

Operating system 112 provides an environment for processor 102 to execute a program. Measurement program 114 implements a film thickness measurement method or a refractive index measurement method according to the present embodiment as will be described later. Two-dimensional image data 116 is data obtained by imaging portion 16 of measurement optical system 10. Measurement result 118 includes a result obtained by execution of measurement program 114.

Communication interface 120 mediates data transmission between processing device 100 and measurement optical system 10, obtains two-dimensional image data from measurement optical system 10, or gives various instructions to measurement optical system 10. Network interface 122 mediates data transmission between processing device 100 and an external server, transmits a measurement result or the like to the server, or receives a program from the server.

Medium drive 124 reads necessary data from a recording medium 126 (for example, an optical disc) which stores a program to be executed by processor 102 and has the data stored in storage 110. Measurement program 114 to be executed by processing device 100 may be installed through recording medium 126 or downloaded from a server through network interface 122.

Measurement program 114 may call in a prescribed sequence at prescribed timing, a necessary module from among program modules provided as a part of operating system 112 to have processing performed. In such a case, measurement program 114 without including such a module is also encompassed in the technical scope of the present invention. Measurement program 114 may be provided as being incorporated as a part of another program.

Functions provided by execution of measurement program 114 by processor 102 of processing device 100 may be performed in the entirety or in part by dedicated hardware.

C. Overview of Method of Measuring Optical Characteristics

Overview of a method of measuring optical characteristics with the optical measurement apparatus including the imaging spectroscope shown in FIG. 1 or 2 will now be described. The optical measurement apparatus according to the present embodiment measures optical characteristics such as an in-plane film thickness distribution of sample S with two-dimensional image 150 including wavelength information and position information.

In measuring an in-plane film thickness distribution of sample S with the imaging spectroscope, a plurality of measurement points are linearly arranged, and hence positional relation with respect to measurement optical system 10 is different among measurement points.

Figure 6:
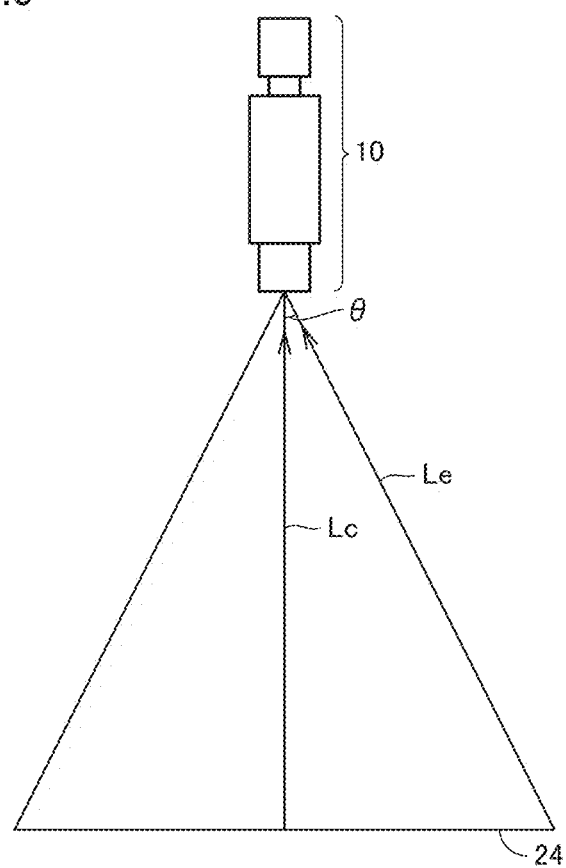
FIG. 6 is a diagram for illustrating incidence of measurement interference light on the measurement optical system of the optical measurement apparatus according to the present embodiment.

FIG. 6 is a diagram for illustrating incidence of measurement interference light on measurement optical system 10 of the optical measurement apparatus according to the present embodiment. Referring to FIG. 6, measurement interference light Lc from a central portion of measurement line 24 produced on sample S propagates through an optical path substantially similar to the optical axis of measurement optical system 10. On the other hand, measurement interference light Le from an end portion of measurement line 24 is incident on measurement optical system 10 at a certain angle of incidence θ. Information which appears in two-dimensional image 150 is different between measurement points on measurement line 24 due to the presence of such angle of incidence θ.

Therefore, in the method of measuring optical characteristics according to the present embodiment, angle of incidence θ at the time when measurement interference light from sample S is incident on measurement optical system 10 is taken into consideration. In measurement of an in-plane film thickness distribution of sample S, substantially, information in the position direction of two-dimensional image 150 output from measurement optical system 10 is corrected. More specifically, as will be described later, processing device 100 calculates a modification factor depending on an angle of incidence on measurement optical system 10 from each measurement point in association with a region in two-dimensional image 150 corresponding to each measurement point in a measurement target irradiated with measurement light. Processing device 100 then calculates optical characteristics of sample S by applying the corresponding modification factor to each pixel value included in two-dimensional image 150.

Depending on sample S, a refractive index of sample S has wavelength characteristics. In this case, such wavelength characteristics are taken into consideration. In measuring an in-plane film thickness distribution of sample S, substantially, information in the wavelength direction of two-dimensional image 150 output from measurement optical system 10 may be corrected.

For the sake of convenience of description, a method of measuring optical characteristics taking into consideration both of (1) influence by an angle of incidence of measurement interference light and (2) wavelength characteristics of a refractive index of sample S will be described in detail, however, (2) wavelength characteristics of a refractive index of sample S do not have to be taken into consideration in some cases.

A film thickness measurement method of measuring a film thickness of sample S (alternatively, an in-plane film thickness distribution) and a refractive index measurement method of measuring a refractive index of sample S will be described below as typical examples of the method of measuring optical characteristics according to the present embodiment. The method of measuring optical characteristics according to the present embodiment is applicable not only to measurement of a film thickness and/or a refractive index but also to measurement of any optical characteristics.

D. Theoretical Explanation of Film Thickness Measurement Method

A film thickness measurement method according to the present embodiment will now theoretically be explained.

Figure 7A:
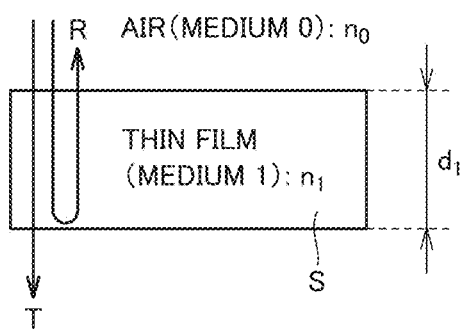
FIGS. 7A and 7B are diagrams for illustrating principles of a film thickness measurement method according to the present embodiment.
Figure 7B:
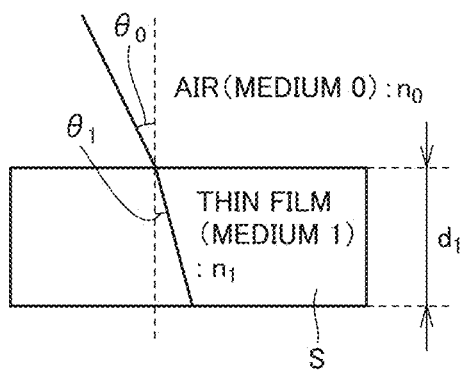

FIGS. 7A and 7B are diagrams for illustrating principles of the film thickness measurement method according to the present embodiment. Referring to FIG. 7A, an example in which a sample of a thin film (having a film thickness $d_1$) is arranged in air (a medium 0) is considered. An intensity transmittance T(1−R) and an intensity reflectance R in consideration of multiple reflection caused in sample S (a medium 1) are as shown in formulae (1) and (2) below, respectively.

$$T = \frac{(1 - r_{01}^2)^2}{1 + r_{01}^4 - 2r_{01}^2 \cos 2\beta_1} \quad (1)$$

$$R = \frac{2r_{01}^2(1 - \cos 2\beta_1)}{1 + r_{01}^4 - 2r_{01}^2 \cos 2\beta_1} \quad (2)$$

$n_1$ represents a refractive index of sample S (medium 1), $n_0$ represents a refractive index of air (medium 0), and $\lambda$ represents a wavelength. In the formulae above, an amplitude reflectance $r_{01}$ represents an amplitude reflectance in an optical path of medium 0→medium 1→medium 0. A phase difference factor $\beta_1$ produced as a result of propagation of light through sample S shown in FIG. 7A can be expressed as in a formula (3) below.

$$\beta_1 = \frac{2\pi n_1 d_1 \cos \theta_1}{\lambda} \quad (3)$$

As shown in FIG. 7B, in consideration of an example in which an angle of incidence of light on sample S is denoted as $\theta_0$, an angle of refraction of light produced in sample S is denoted as $\theta_1$. Relation of $n_0 \cdot \sin \theta_0 = n_1 \cdot \sin \theta_1$ (Snell's law) is satisfied between angle of incidence $\theta_0$ and angle of refraction $\theta_1$. A wave number $K_1$ as shown in a formula (4) below is introduced by using relation between angle of incidence $\theta_0$ and angle of refraction $\theta_1$. Wave number $K_1$ corresponds to a parameter for facilitating Fourier transform for measuring a film thickness. With wave number $K_1$, a phase angle $\beta_1$ in sample S can be defined as shown in a formula (5) below.

$$K_1 \equiv \frac{2\pi n_1 \cos \theta_1}{\lambda} = \frac{2\pi n_1}{\lambda} \sqrt{1 - \left(\frac{n_0}{n_1} \sin \theta_0\right)^2} \quad (4)$$

$$\beta_1 = K_1 d_1 \quad (5)$$

Wave number $K_1$ shown in the formula (4) above includes angle of incidence $\theta_0$, and a film thickness in consideration of a difference in angle of incidence $\theta_0$ corresponding to each measurement point can be calculated by using such wave number $K_1$.

Considering Fourier transform with respect to phase angle $\beta_1$, $\cos 2\beta_1$ representing a phase factor is non-linear with respect to intensity reflectance R, and fast Fourier transform (FFT) cannot be applied as it is. Then, after conversion to a function with linearity with respect to phase factor $\cos 2\beta_1$ by introducing a specific variable, Fourier transform is performed. By way of example, a wave-number-converted transmittance T'(≡1/T) or a wave-number-converted reflectance R'(≡R/(1−R)) which is a linear formula with respect to phase factor $\cos 2\beta_1$ is introduced. Specifically, wave-number-converted transmittance T' and wave-number-converted reflectance R' are derived from the formulae (1) and (2) above as in formulae (6) and (7) below.

$$T' = \frac{1 + r_{01}^4}{(1 - r_{01}^2)^2} - \frac{2r_{01}^2}{(1 - r_{01}^2)^2} \cos 2\beta_1 \equiv T_a + T_b \cos 2K_1 d_1 \quad (6)$$

$$R' = \frac{2r_{01}^2}{(1 - r_{01}^2)^2}(1 - \cos 2\beta_1) \equiv R_a + R_b \cos 2K_1 d_1 \quad (7)$$

Furthermore, in a power spectrum $P(K_1)$ obtained through Fourier transform of wave-number-converted transmittance T' shown in the formula (6) or wave-number-converted reflectance R' shown in the formula (7) above, a peak appears at a position corresponding to film thickness $d_1$ of sample S. By calculating a position of a peak which appears in power spectrum $P(K_1)$, film thickness $d_1$ of sample S is determined.

Reference is to be made to Japanese Patent Laying-Open No. 2009-092454 for details of wave-number-converted transmittance T' and wave-number-converted reflectance R'.

Thus, a modification factor depending on an angle of incidence on the measurement optical system from each measurement point includes wave number $K_1$ representing a parameter including wavelength $\lambda$ of measurement light and refractive index $n_1$ of sample S. Wave number $K_1$ may be calculated in consideration of wavelength-dependency of a refractive index of sample S. Then, a film thickness d is determined through Fourier transform with respect to a row of corresponding wave numbers $K_1(i, j)$, of a row of values resulting from conversion in accordance with a relational expression (for example, R/(1−R) or 1/T) for linearizing a pixel value of a two-dimensional image corresponding to a measurement point of interest with respect to a phase factor (a wave-number-converted transmittance distribution T'(i, j) or a wave-number-converted reflectance distribution R'(i, j)).

As set forth above, when angle of incidence $\theta_0$ of measurement interference light on sample S cannot be regarded as zero, a film thickness of sample S in consideration of influence by angle of incidence $\theta_0$ can be calculated by introducing wave number $K_1$ including angle of incidence $\theta_0$.

A method of calculating angle of incidence $\theta_0$ will now be described. As described above, in the film thickness measurement method according to the present embodiment, angle of incidence $\theta_0$ corresponding to each measurement point should be calculated. Each measurement point can be set for each pixel or a set of pixels which is a set of a plurality of adjacent pixels in two-dimensional image 150 output from measurement optical system 10.

Figure 8A:
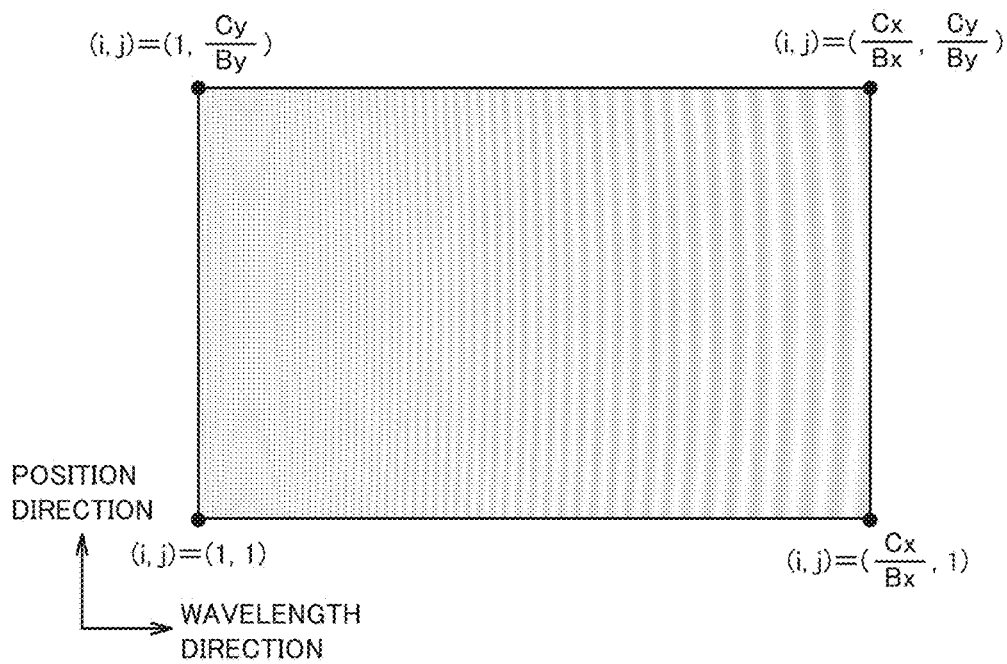
FIGS. 8A and 8B are diagrams showing examples of a two-dimensional image handled in the optical measurement apparatus according to the present embodiment.
Figure 8B:
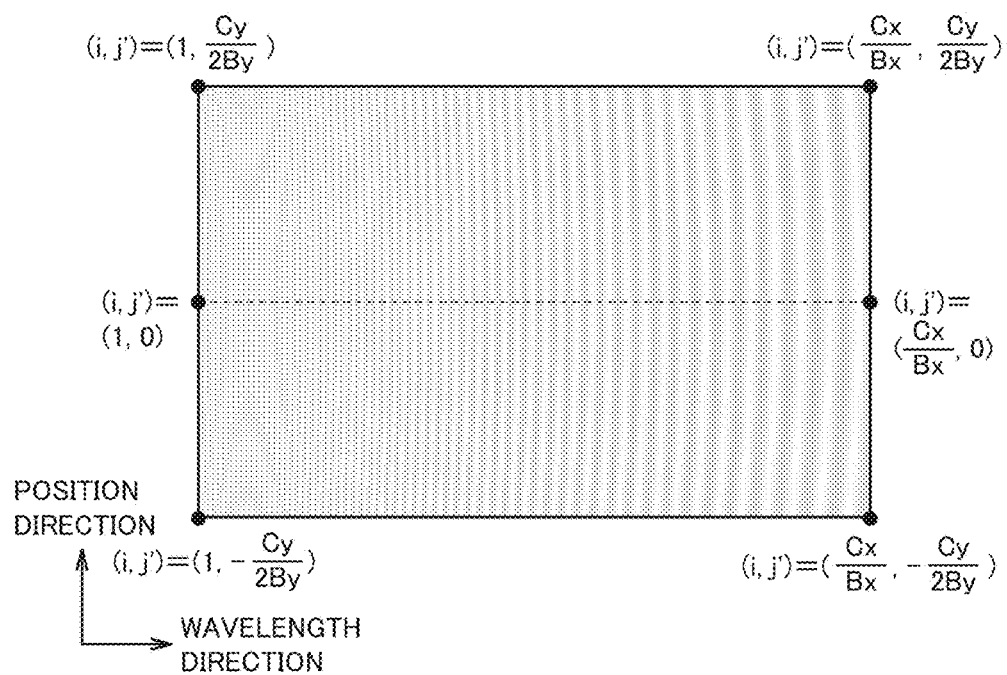

FIGS. 8A and 8B are diagrams showing examples of two-dimensional image 150 handled in the optical measurement apparatus according to the present embodiment. Since the light reception surface of imaging device 160 and two-dimensional image 150 are in a one-to-one correspondence, a coordinate representing any position on the light reception surface of imaging device 160 indicates a corresponding position in two-dimensional image 150.

Essentially, angle of incidence $\theta_0$ should be calculated for a position corresponding to each channel of imaging device 160. When the number of channels of imaging device 160 is sufficiently large for an angle of view $\phi$ of measurement optical system 10, a set of adjacent channels may be regarded as one pixel of two-dimensional image 150, and angle of incidence $\theta_0$ may be calculated for each pixel. Gathering of such a plurality of adjacent channels is referred to as "binning" below.

FIG. 9 is a diagram for illustrating binning processing in calculating angle of incidence $\theta_0$ used in the film thickness measurement method according to the present embodiment. As shown in FIG. 9, a prescribed number of adjacent channels arranged in the position direction among a plurality of channels constituting imaging device 160 are processed together. Imaging device 160 has a resolution of $C_x$ channels×$C_y$ channels, and can output two-dimensional image 150 corresponding to this number of channels. By gathering adjacent channels, processing is accelerated.

The number of channels gathered in the position direction is referred to as a "binning factor $B_y$." Binning factor $B_y$ is preferably a common divisor of the number of channels $C_y$. By setting binning factor $B_y$ to "1", angle of incidence $\theta_0$ in accordance with the number of channels of imaging device 160 is calculated.

Though FIG. 9 shows an example in which a plurality of channels in the position direction are set as one pixel, a plurality of channels also in the wavelength direction may be set as one pixel. Namely, a binning factor $B_x$ in the wavelength direction may be introduced.

In the description below, a position of any pixel among a plurality of pixels defined in two-dimensional image 150 is defined based on combination of a wavelength-direction pixel number (represented below as a "variable i") and a position-direction pixel number (represented by a "variable j" or a "variable j'" below). Position-direction pixel number j is expressed with an integer which satisfies a condition of $1 \leq j \leq C_y/B_y$.

FIG. 8A shows a coordinate system when the lower left of the sheet plane is defined as the origin coordinate (1, 1). In this case, a coordinate at the upper right of the sheet plane is defined as ($C_x/B_x$, $C_y/B_y$). FIG. 8B shows a coordinate system when the center in the position direction is defined as the origin coordinate (1, 0). In the coordinate system shown in FIG. 8B, angle of incidence $\theta_0$ corresponding to a pixel at the center in the position direction, that is, on a straight line connecting the coordinate (1, 0) and a coordinate ($C_x/B_x$, 0) to each other is zero. Relation of $j'=j-C_y/2B_y$ is satisfied between position-direction pixel number j' and position-direction pixel number j.

The coordinate system shown in FIG. 8A is advantageous in simplification of processing of wavelength information and position information included in two-dimensional image 150, and the coordinate system shown in FIG. 8B is advantageous in simplification of processing in calculation of angle of incidence $\theta_0$ corresponding to each measurement point.

Angle of incidence $\theta_0$ at a measurement point corresponding to position-direction pixel number j (or position-direction pixel number j') of two-dimensional image 150 will be reviewed below.

Figure 10:
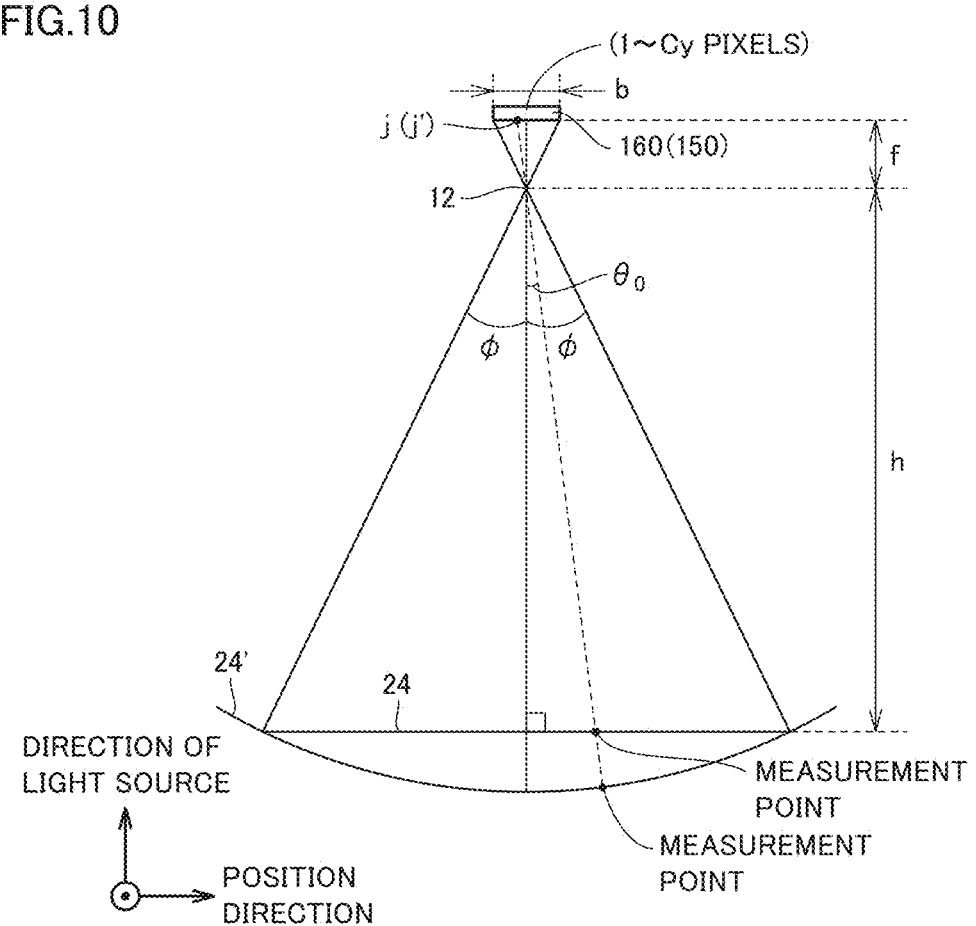
FIG. 10 is a diagram for illustrating a method of calculating an angle of incidence used in the film thickness measurement method according to the present embodiment.

FIG. 10 is a diagram for illustrating a method of calculating angle of incidence $\theta_0$ used in the film thickness measurement method according to the present embodiment. FIG. 10 shows an example in which a measurement line is regarded as an arc (a measurement line 24') and an example in which the measurement line is regarded as a straight line (measurement line 24) in transmissive optical measurement apparatus 1 shown in FIG. 1 by way of example. Angle of incidence $\theta_0$ is calculated with any example being adopted.

In FIG. 10, b represents a length of imaging device 160 in the position direction, f represents a focal length of object lens 12, and h represents a height h of object lens 12. Length b, focal length f, and height h are expressed with the same unit (for example, mm). $\phi$ represents angle of view $\phi$ of measurement optical system 10 (=A tan(b/2f)).

When the measurement line is regarded as the arc (measurement line 24'), angle of incidence $\theta_0$ corresponding to position-direction pixel number j' is derived as in a formula (8-1) below. The formula (8-1) defines angle of incidence $\theta_0$ by using position-direction pixel number j' when angle of view $\phi$ and the center in the position direction are set to zero. A formula (8-2) can be derived by deforming the formula (8-1) with a relational expression ($\phi$=A tan(b/2f)) for angle of view $\phi$ and a relational expression ($j'=j-C_y/2B_y$) for the position-direction pixel number.

$$\theta_0(j') = j' \cdot \frac{2B_y}{C_y} \cdot \phi \tag{8-1}$$

$$\theta_0(j) = \frac{2B_y}{C_y}\left(j - \frac{C_y}{2B_y}\right) \cdot \tan^{-1}\left(\frac{b}{2f}\right) \tag{8-2}$$

Alternatively, when the measurement line is regarded as the straight line (measurement line 24), angle of incidence $\theta_0$ corresponding to position-direction pixel number j' is derived as in a formula (9-1) below. The formula (9-1) defines angle of incidence $\theta_0$ by using position-direction pixel number j' when angle of view $\phi$ and the center in the position direction are set to zero. A formula (9-2) can be derived by deforming the formula (9-1) by using the relational expression ($\phi$=A tan(b/2f)) for angle of view $\phi$ and the relational expression ($j'=j-C_y/2B_y$) for the position-direction pixel number.

$$\theta_0(j') = \tan^{-1}\left(\frac{2\tan\phi}{C_y} \cdot j'\right) \tag{9-1}$$

-continued $$\theta_0(j) = \tan^{-1}\left\{\frac{b}{C_y f}\left(j - \frac{C_y}{2B_y}\right)\right\} \quad (9\text{-}2)$$

In the formulae (8-1), (8-2), (9-1), and (9-2) above, each channel of imaging device 160 is handled as a point with its magnitude being ignored. Though observed transmitted light or reflected light should be expressed with a value resulting from integration of changes in angle corresponding to magnitude of one channel in a strict sense, magnitude of one channel is sufficiently smaller than a length of a range of imaging, and change in angle is ignorable. Therefore, transmitted light or reflected light can be represented by a value for transmitted light or reflected light from one point.

A formula (10) below can be derived by defining wave number $K_1$ with wavelength-direction pixel number i and position-direction pixel number j of a two-dimensional image, with $n_0=1$ (a refractive index of air) being set, in the formula (4) above.

$$K_1(i, j) = \frac{2\pi n_1(i, j)}{\lambda(i, j)}\sqrt{1 - \left(\frac{\sin\theta_0(j)}{n_1(i, j)}\right)^2} \quad (10)$$

In the formula (10), a wavelength conversion formula $\lambda(i, j)$ representing relation between a position of a pixel in two-dimensional image 150 and a wavelength can be determined in advance by wavelength calibration of measurement optical system 10. Wavelength calibration includes an operation to allocate a value for corresponding wavelength $\lambda$ to each wavelength-direction pixel number i, for each position-direction pixel number j.

A refractive index $n_1(i, j)$ of sample S (that is, refractive index $n_1(\lambda)$) can be obtained in advance with a measurement apparatus capable of optical constant analysis (for example, a thickness monitor based on microscopic spectrophotometry). In the formula (10), angle of incidence $\theta_0(j)$ corresponding to each measurement point is defined in accordance with the formula (8-2) or (9-2) above. By substituting this value into the formula (10), wave number $K_1(i, j)$ at a pixel position (i, j) can be determined. Wave number $K_1$ is thus calculated for each pixel position (i, j) in the two-dimensional image in consideration of magnitude of corresponding angle of incidence $\theta_0(j)$.

A film thickness in consideration of both of (1) influence by an angle of incidence of measurement interference light and (2) wavelength characteristics of a refractive index of sample S can be determined based on relation between wave number $K_1(i, j)$ at pixel position (i, j) and an actually measured value.

In a more specific calculation procedure, the optical measurement apparatus according to the present embodiment is used to obtain a transmittance distribution T(i, j) or a reflectance distribution R(i, j) of sample S. In succession, wave number distribution characteristics in which the abscissa represents wave number $K_1(i, j)$ and the ordinate represents a wave-number-converted transmittance distribution T'(i, j) or a wave-number-converted reflectance distribution R'(i, j) are generated for each position-direction pixel number j. Power spectrum $P(K_1)$ is calculated by subjecting the generated wave number distribution characteristics to Fourier transform, and a film thickness distribution (an in-plane film thickness distribution) of sample S in consideration of wavelength-dependency of an angle of incidence and a refractive index can be determined based on a peak which appears in calculated power spectrum $P(K_1)$.

As described above, wave number $K_1$ is calculated for each pixel position (i, j) in an imaging device including a two-dimensional light reception surface in accordance with the formula above, based on angle of incidence $\theta_0(j)$ at each measurement point on the measurement line, refractive index $n_1(\lambda)$ in consideration of a wavelength dispersion, and wavelength $\lambda$. Then, wave-number-converted transmittance distribution T'(i, j) or wave-number-converted reflectance distribution R'(i, j) is generated from transmittance distribution T(i, j) or reflectance distribution R(i, j) of sample S obtained by actual measurement, by using a relational expression for linearization with respect to phase factor cos 2β (for example, R/(1−R) or 1/T). By applying wave number $K_1(i, j)$ to such generated wave-number-converted transmittance distribution T' or wave-number-converted reflectance distribution T', a power spectrum P(m, j) subjected to Fourier transform (a parameter m representing a discrete value corresponding to the abscissa of the power spectrum) can be obtained. A value for a film thickness at each measurement point of sample S is calculated based on a peak which appears in power spectrum P(m, j).

Typically, any of a method of using discrete Fourier transform such as fast Fourier transform (FFT) and an optimization method such as a maximum entropy method (which is also referred to as "MEM" below) can be adopted as a method of specifying a wave number component large in amplitude (a peak) from wave number distribution characteristics. When discrete Fourier transform is employed, a power of two such as 512, 1024, 2048, 4096, . . . is used as a discrete value in a frequency domain.

E. Specific Example of Film Thickness Measurement Method

A method of measuring a film thickness based on the theoretical explanation of the film thickness measurement method described above will now be described. In the description below, a method of determining a film thickness of sample S based on a peak which appears in power spectrum $P(K_1)$ obtained by subjecting wave-number-converted transmittance T' or wave-number-converted reflectance R' to Fourier transform (what is called the FFT method) and a method of determining a film thickness of sample S by shape comparison (fitting) between obtained wavelength distribution characteristics (an actually measured value of a transmittance spectrum or a reflectance spectrum) and wavelength distribution characteristics calculated with a model formula (a theoretical formula) including an angle of incidence, a refractive index, a wavelength, and a film thickness as parameters (what is called an optimization method) will be described.

Though any one of these film thickness measurement methods may be incorporated, the film thickness measurement method is preferably selectable as appropriate depending on a film thickness or a material for sample S.

(e1: Processing Procedure (No. 1) in Film Thickness Measurement Method)

A processing procedure (No. 1) in the film thickness measurement method according to the present embodiment will initially be described. The processing procedure (No. 1) in the film thickness measurement method is a method of determining a film thickness of sample S based on a peak which appears in power spectrum $P(K_1)$ with respect to wave number $K_1$.

Figure 11:
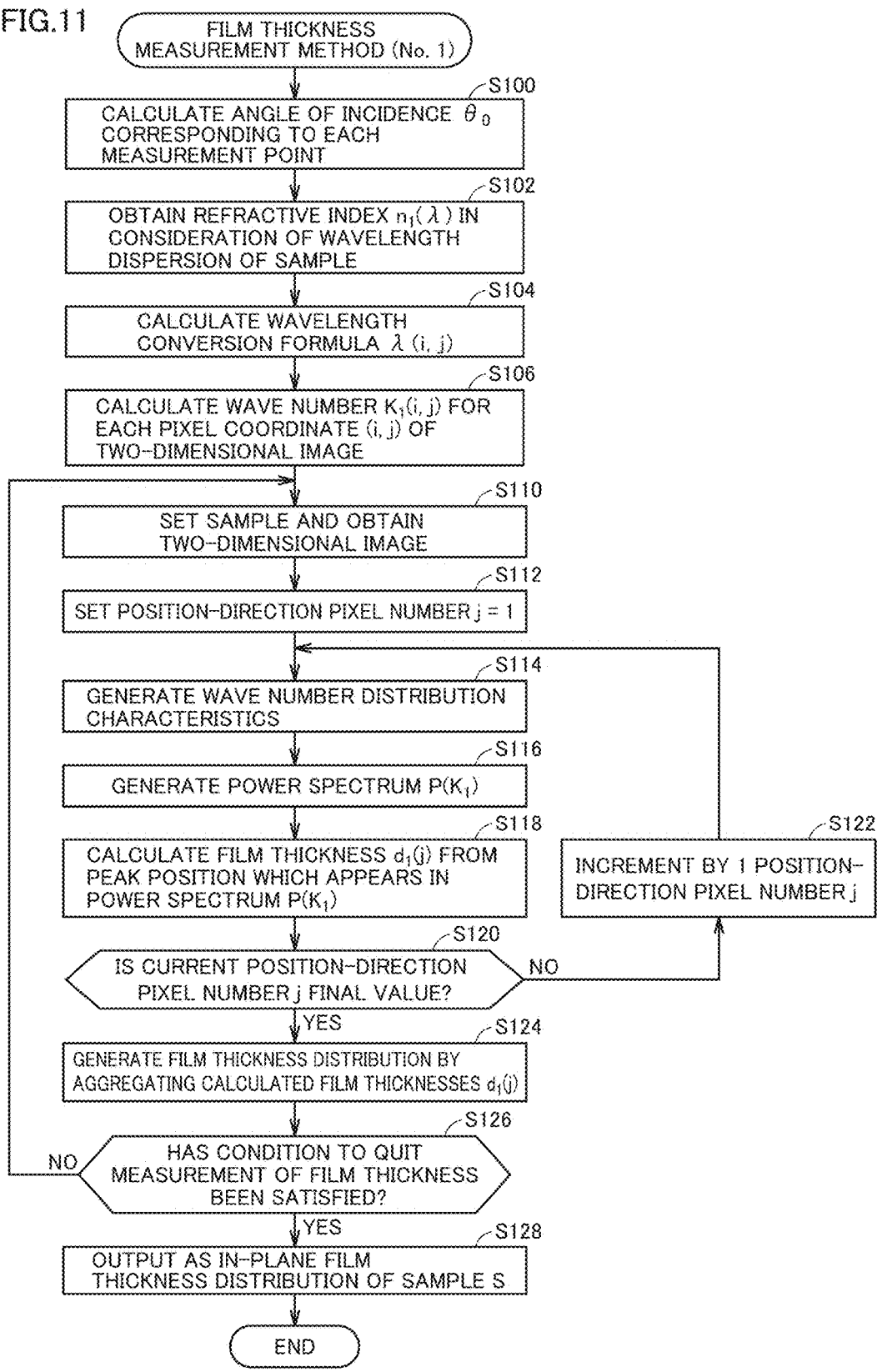
FIG. 11 is a flowchart showing a processing procedure (No. 1) in the film thickness measurement method according to the present embodiment.
Figure 12:
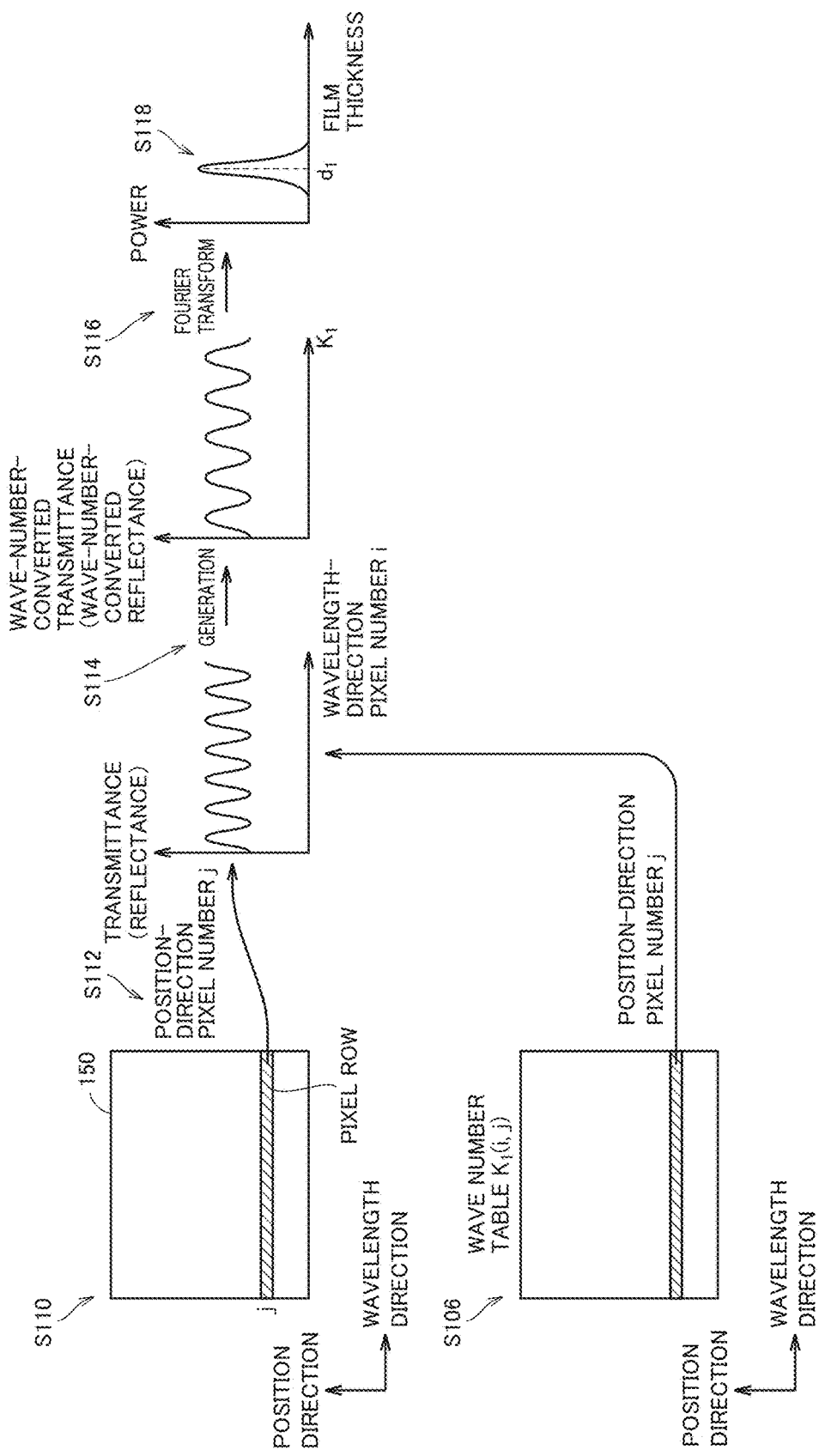
FIG. 12 is a diagram for illustrating processing contents in the processing procedure (No. 1) in the film thickness measurement method shown in FIG. 11.

FIG. 11 is a flowchart showing the processing procedure (No. 1) in the film thickness measurement method according to the present embodiment. FIG. 12 is a diagram for illustrating processing contents in the processing procedure (No. 1) in the film thickness measurement method shown in FIG. 11.

Referring to FIG. 11, initially, processing device 100 calculates angle of incidence $\theta_0$ corresponding to each measurement point, of measurement interference light incident on measurement optical system 10 (step S100).

Specifically, processing device 100 calculates angle of incidence $\theta_0$ corresponding to each measurement point set on the measurement line (corresponding to each pixel in the position direction of two-dimensional image 150 determined depending on the number of channels and the binning factor of imaging device 160) for each position-direction pixel number j. Namely, processing device 100 calculates $\theta_0(j)$ in the formula (10) above for all position-direction pixel numbers j. $\theta_0(j)$ may be a radian value or a value of a trigonometric function (for example, $\sin \theta_0(j)$ or $\cos \theta_0(j)$). Any value adapted to subsequent operation processing may be adopted so long as the value represents magnitude of an angle of incidence.

A value of angle of incidence $\theta_0$ corresponding to each measurement point obtained as a result of step S100 does not have to be calculated again, so long as the setting or the configuration of the optical measurement apparatus is the same. Therefore, when angle of incidence $\theta_0$ corresponding to each measurement point has been calculated in advance, processing in step S100 may be skipped.

Processing device 100 obtains refractive index $n_1(\lambda)$ in consideration of wavelength dispersion of sample S based on a result of measurement for sample S with a measurement apparatus capable of optical constant analysis (for example, a thickness monitor based on microscopic spectrophotometry) (step S102).

Refractive index $n_1(\lambda)$ of sample S obtained in step S102 does not have to be obtained again so long as a material for sample S is the same. Therefore, so long as identity of sample S corresponding to refractive index $n_1(\lambda)$ obtained earlier is maintained, processing in step S102 may be skipped. When a refractive index can be regarded as constant regardless of a wavelength, a constant value may be set for refractive index $n_1(\lambda)$.

Processing device 100 calculates a wavelength conversion formula $\lambda(i, j)$ representing relation between a pixel position in two-dimensional image 150 and wavelength $\lambda$ based on a result of wavelength calibration for measurement optical system 10 (step S104). In step S104, wavelength $\lambda$ is brought in correspondence with pixel position (i, j) in two-dimensional image 150. Wavelength $\lambda$ can be expressed in matrix with pixel position (i, j) in two-dimensional image 150 being defined as a parameter (that is, wavelength $\lambda=\lambda(i, j)$).

Basically, wavelength conversion formula $\lambda(i, j)$ calculated in step S104 does not have to be calculated again so long as the setting or the configuration of measurement optical system 10 is the same. Therefore, so long as wavelength conversion formula $\lambda(i, j)$ calculated earlier can effectively be made use of, processing in step S104 may be skipped.

The order of performing processing in steps S100, S102, and S104 is not particularly limited. Timing to perform processing in steps S100, S102, and S104 may be different.

In succession, processing device 100 expands wave number $K_1$ shown in the formula (4) above for pixel position (i, j) in two-dimensional image 150. Processing device 100 calculates wave number $K_1(i, j)$ for each pixel position (i, j) in two-dimensional image 150 (step S106).

As shown in the formula (4) above, in the film thickness measurement method according to the present embodiment, wave number $K_1$ which takes wavelength $\lambda$, refractive index $n_1$, and angle of incidence $\theta_0$ as variables is introduced.

Among the variables included in wave number $K_1$, refractive index $n_1$ is a function of wavelength $\lambda$. Since wavelength $\lambda$ can be defined by wavelength conversion formula $\lambda(i, j)$, refractive index $n_1$ can be defined with pixel position (i, j) in two-dimensional image 150 being defined as a parameter (that is, refractive index $n_1=n_1(\lambda)=n_1(i, j)$ and wavelength $\lambda=\lambda(i, j)$). Angle of incidence $\theta_0$ corresponding to each measurement point which is calculated in step S100 can be used as angle of incidence $\theta_0$. Angle of incidence $\theta_0$ is defined only by position-direction pixel number j (that is, angle of incidence $\theta_0=\theta_0(j)$).

As set forth above, since all of wavelength $\lambda$, refractive index $n_1$, and angle of incidence $\theta_0$ can be defined with measurement point (i, j) corresponding to each pixel in two-dimensional image 150, a value of each of them is uniquely determined by designating pixel position (i, j). Processing device 100 generates wave number $K_1(i, j)$ representing a value of wave number $K_1$ for each pixel position (i, j) by applying values for wavelength $\lambda$, refractive index $n_1$, and angle of incidence $\theta_0$ determined for each pixel position (i, j). As shown in FIG. 12, generated wave number $K_1(i, j)$ corresponds to each pixel in two-dimensional image 150.

Processing in steps S100 to S106 above corresponds to a preparation step.

Sample S is set in optical measurement apparatus 1, and processing device 100 obtains two-dimensional image 150 imaged while sample S is irradiated with measurement interference light (step S110). Processing device 100 obtains an actually measured value of transmittance distribution T(i, j) (or reflectance distribution R(i, j)) for a plurality of measurement points on measurement line 24 of sample S. As shown in FIG. 12, two-dimensional image 150 having the wavelength direction and the position direction is obtained. The wavelength direction corresponds to wavelength $\lambda$ for specific position-direction pixel number j.

In succession, processing device 100 sets position-direction pixel number j=1 (step S112). Setting of position-direction pixel number j means setting a pixel row corresponding to specific position-direction pixel number j in two-dimensional image 150 as a target as shown in FIG. 12.

Processing device 100 generates wave number distribution characteristics in which the abscissa represents wave number $K_1(i, j)$ and the ordinate represents wave-number-converted transmittance distribution T'(i, j) (or wave-number-converted reflectance distribution R'(i, j)) from obtained transmittance distribution T(i, j) (or reflectance distribution R(i, j)) by referring to wave number $K_1(i, j)$ calculated in step S106 (step S114).

More specifically, as shown in FIG. 12, processing device 100 extracts values in a row corresponding to current position-direction pixel number j from wave number $K_1(i, j)$ and applies the values to values of a pixel row extracted from two-dimensional image 150.

Processing device 100 thus converts obtained wavelength distribution characteristics (correspondence between each wavelength and a value of a transmittance or a reflectance at that wavelength) into correspondence with a converted value of the transmittance or the reflectance calculated in accordance with wave number distribution characteristics. The wave number distribution characteristics include correspondence between a wave number determined by a function including an angle of incidence, a refractive index, and a wavelength as parameters and a value of a transmittance or a reflectance at that wave number. Alternatively, the wave number distribution characteristics include correspondence between a wave number and a converted value of the transmittance or the reflectance calculated in accordance with a relational expression for linearization with respect to phase factor cos 2β (for example, R/(1−R) or 1/T).

In succession, processing device 100 generates power spectrum $P(K_1)$ by subjecting the wave number distribution characteristics generated in step S114 in which the abscissa represents wave number $K_1(i, j)$ to Fourier transform with respect to wave number $K_1(i, j)$ (step S116). Processing device 100 subjects a row of values resulting from conversion in accordance with a relational expression for linearization of pixel values of two-dimensional image 150 corresponding to a measurement point of interest with respect to a phase factor to Fourier transform with respect to a row of corresponding wave numbers.

Processing device 100 calculates film thickness $d_1(j)$ at a measurement point corresponding to current position-direction pixel number j by calculating a peak position which appears in power spectrum $P(K_1)$ generated in step S116 (step S118). Processing device 100 determines a film thickness at a measurement point of interest based on a peak position which appears in power spectrum $P(K_1)$ obtained through Fourier transform. A wave number component (that is, film thickness $d_1(j)$) large in amplitude may be determined by using the optimization method instead of Fourier transform.

Processing device 100 determines whether or not current position-direction pixel number j is a final value (step S120). When current position-direction pixel number j is not the final value (NO in step S120), processing device 100 increments current position-direction pixel number j by one (step S122) and repeats processing in step S114 or later.

When current position-direction pixel number j is the final value (YES in step S120), processing device 100 generates a film thickness distribution on measurement line 24 of sample S by aggregating film thicknesses $d_1(j)$ calculated at position-direction pixel numbers j from 1 to the final value (step S124). Processing device 100 aggregates the film thicknesses determined for a plurality of measurement points and outputs the resultant aggregate as the film thickness distribution.

Processing device 100 determines whether or not a condition to quit measurement of a film thickness of sample S has been satisfied (step S126). When the condition to quit measurement of a film thickness of sample S has not been satisfied (NO in step S126), processing device 100 repeats the processing in step S110 or later.

In contrast, when the condition to quit measurement of a film thickness of sample S has been satisfied (YES in step S126), processing device 100 integrates film thickness distributions successively calculated in step S124 and outputs the resultant film thickness distribution as a film thickness distribution (an in-plane film thickness distribution) at the measurement surface of sample S (step S128). Then, the process ends.

In the processing procedure (No. 1) in the film thickness measurement method described above, description has been given with attention being paid to wave number $K_1$ as a modification factor depending on angle of incidence $\theta_0$ on measurement optical system 10 from a measurement point, however, the modification factor is not limited thereto. For example, the modification factor is a concept which may cover wave-number-converted transmittance $T'(\equiv 1/T)$ or wave-number-converted reflectance $R'(\equiv R/(1-R))$ described above.

(e2: Measurement Example)

A measurement example obtained with the film thickness measurement method (No. 1) according to the present embodiment will now be shown.

Figure 14:
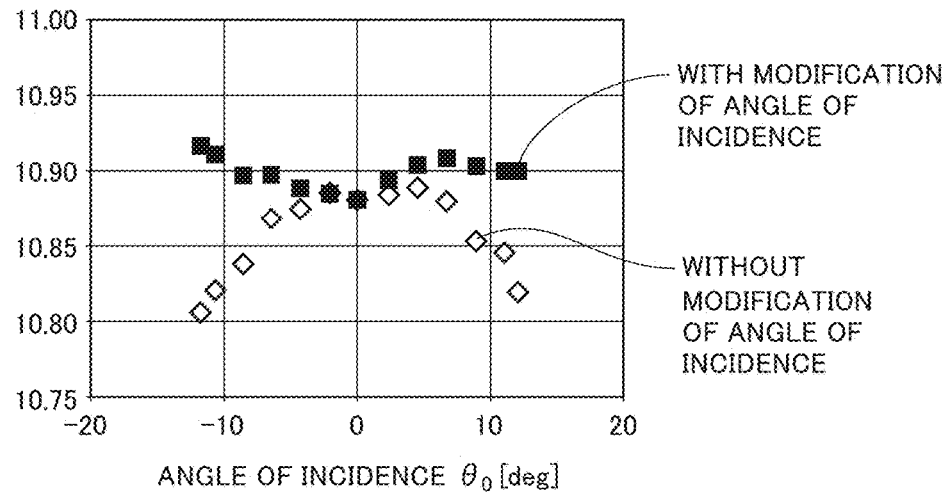
FIG. 14 is a diagram showing one example of a film thickness trend obtained with the film thickness measurement method according to the present embodiment.

FIG. 14 is a diagram showing one example of a film thickness trend obtained with the film thickness measurement method according to the present embodiment. A 1-mm square polyethylene thin film (an outer dimension of 1 mm×1 mm) was employed as sample S.

A film thickness in each of two patterns of with modification (the present embodiment) and without modification of angle of incidence $\theta_0$ was measured, with a measurement point in sample S (that is, angle of incidence $\theta_0$) being sequentially varied. A lens having a focal length f=16 mm was employed as object lens 12.

Figure 13:
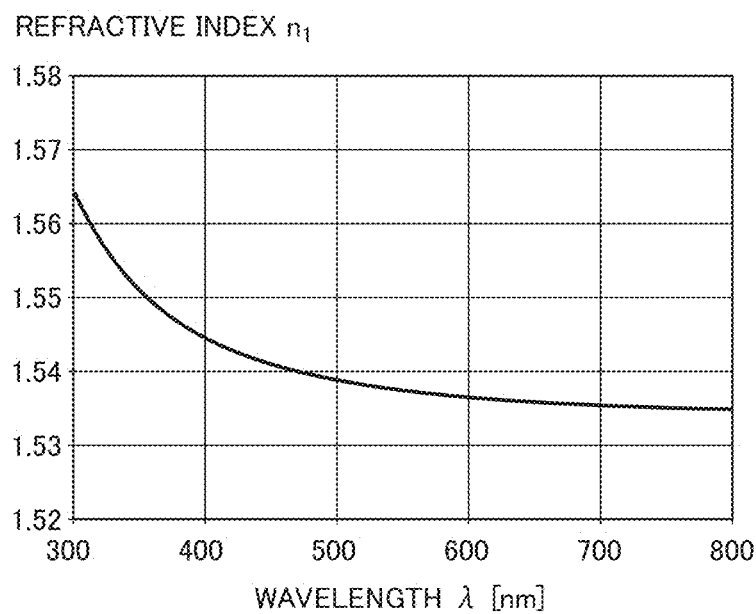
FIG. 13 is a diagram showing one example of a wavelength distribution of a refractive index of a polyethylene thin film.

A wavelength distribution of a refractive index of the polyethylene thin film actually measured with a thickness monitor based on microscopic spectrophotometry was adopted as refractive index $n_1$. FIG. 13 is a diagram showing one example of a wavelength distribution of refractive index $n_1(\lambda)$ of the polyethylene thin film. By way of example, a Cauchy dispersion formula as shown in a formula (11) below is used for refractive index $n_1(\lambda)$ shown in FIG. 13.

$$n_1(\lambda) = C_0 + \frac{C_1}{\lambda^2} + \frac{C_2}{\lambda^4} \quad (11)$$

In the example shown in FIG. 13, coefficients are set as $C_0=1.533731$, $C_1=429.0333$, and $C_2=2.09247\times 10^8$.

FIG. 14 shows variation in measured film thickness with variation in angle of incidence $\theta_0$. As shown in FIG. 14, it can be seen that the film thickness trend becomes flatter by taking into consideration angle of incidence $\theta_0$. It is shown that a film thickness distribution (an in-plane film thickness distribution) of sample S can more accurately be measured.

(e3: Simulation Example)

Figure 15:
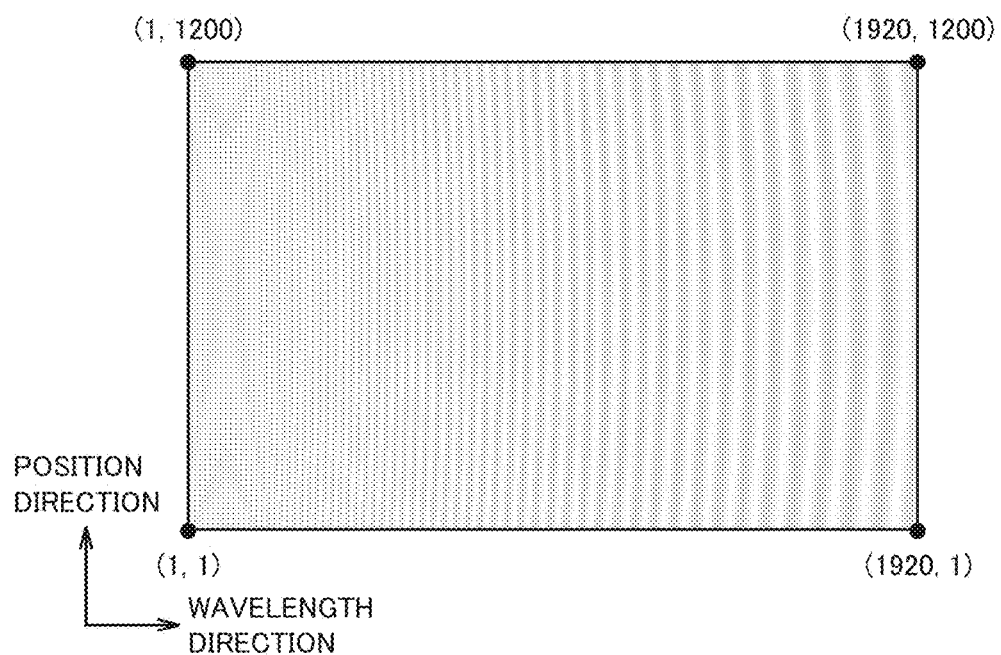
FIG. 15 is a diagram showing one example of a two-dimensional image exhibiting a transmittance spectrum in accordance with a theoretical formula according to the present embodiment.

For example, a theoretical value of transmittance spectrum $T(\lambda)$ at each measurement point can be calculated based on the formulae (1), (5), (8-2), and (10) above. FIG. 15 is a diagram showing one example of a two-dimensional image (1200 pixels×1920 pixels) exhibiting a transmittance spectrum in accordance with a theoretical formula according to the present embodiment. The two-dimensional image exhibiting the transmittance spectrum shown in FIG. 15 is obtained when film thickness $d_1$ is (uniformly) set to 10 [μm] and an amplitude reflectance $|r_{01}|$ is set to 0.2.

A wavelength distribution of a refractive index of the polyethylene thin film actually measured with a thickness monitor based on microscopic spectrophotometry as shown in FIG. 13 described above was adopted as refractive index $n_1$. By way of example, the Cauchy dispersion formula as shown in the formula (11) above is used for refractive index $n_1(\lambda)$ shown in FIG. 13.

In the example shown in FIG. 13, coefficients are set as $C_0=1.533731$, $C_1=429.0333$, and $C_2=2.09247\times 10^8$.

Figure 16:
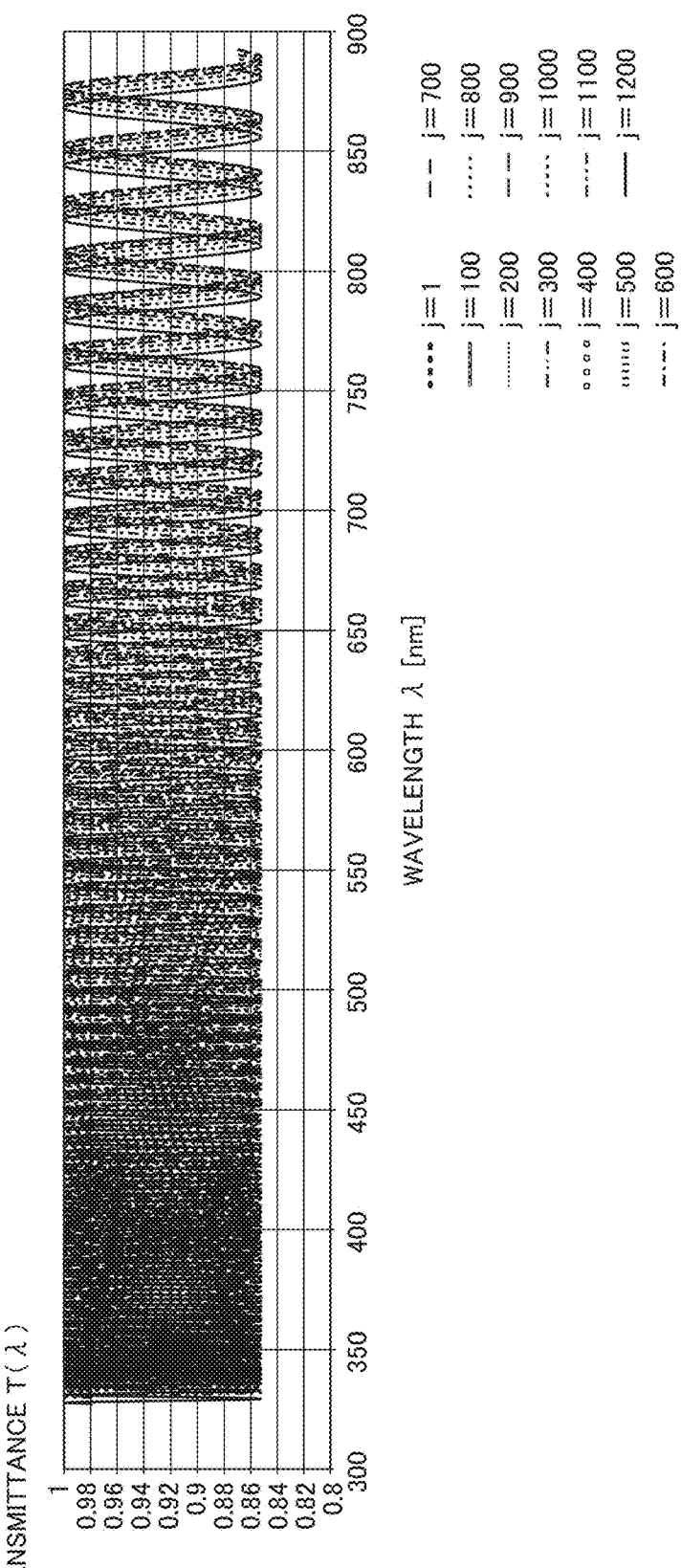
FIG. 16 is a graph showing a transmittance spectrum $T(\lambda)$ corresponding to a position-direction pixel number j in the two-dimensional image (theoretical value) shown in FIG. 15.

FIG. 16 is a graph showing transmittance spectrum $T(\lambda)$ corresponding to position-direction pixel number j in the two-dimensional image (theoretical value) shown in FIG. 15. FIG. 16 shows transmittance spectrum $T(\lambda)$ on a line of each position-direction pixel number j=1, 100, 200, . . . , 1200. The reason why transmittance spectrum $T(\lambda)$ is not consistent in FIG. 16 is because of a difference in angle of incidence $\theta_0$ corresponding to each measurement point.

FIGS. 17A and 17B are graphs showing wave-number-converted transmittances $T'(K_1)$ calculated from transmittance spectrum $T(\lambda)$ shown in FIG. 16. FIG. 17A shows wave-number-converted transmittance $T'(K_1)$ calculated with wave number $K_1$ with angle of incidence $\theta_0$ being assumed as zero for all position-direction pixel numbers j. FIG. 17B shows wave-number-converted transmittance $T'(K_1)$ calculated with wave number $K_1$ in consideration of angle of incidence $\theta_0$ in accordance with all position-direction pixel numbers j.

In transmittance spectrum $T(\lambda)$ shown in FIG. 16, a period of an interference waveform is different owing to a difference in position-direction pixel number j (that is, angle of incidence $\theta_0$). Therefore, it can be seen that wave-number-converted transmittance $T'(K_1)$ is also inconsistent as shown in FIG. 17A when wave number $K_1$ not in consideration of a difference in angle of incidence $\theta_0$ is used.

On the other hand, it can be seen that, by using wave number $K_1$ in consideration of angle of incidence $\theta_0$ in accordance with position-direction pixel number j, wave-number-converted transmittance $T'(K_1)$ is consistent for all position-direction pixel numbers j. Since wave-number-converted transmittance $T'(K_1)$ is substantially the same regardless of position-direction pixel number j, a correct film thickness can be calculated from any wave-number-converted transmittance $T'(K_1)$.

Figure 18:
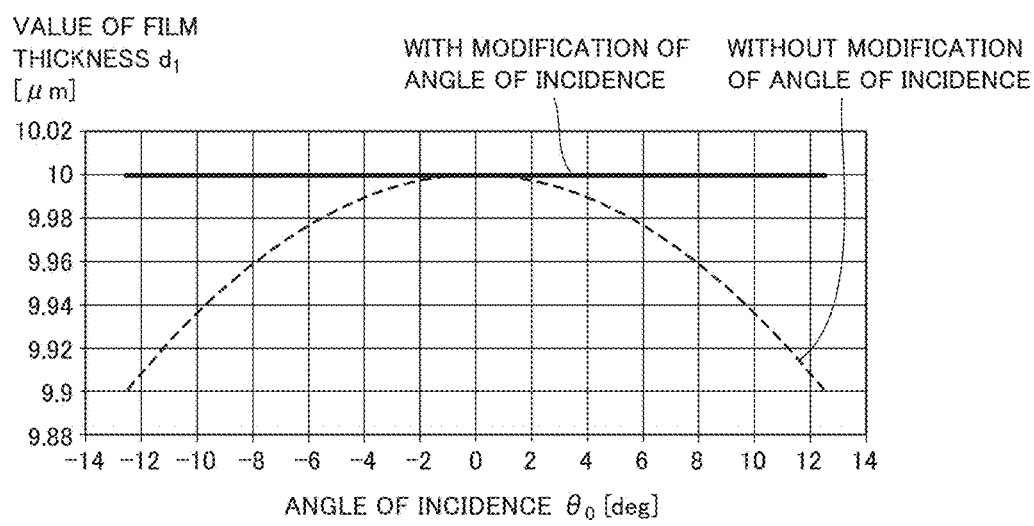
FIG. 18 is a diagram showing one example of a film thickness trend calculated from wave-number-converted transmittance $T'(K_1)$ shown in FIGS. 17A and 17B.

FIG. 18 is a diagram showing one example of a film thickness trend calculated from wave-number-converted transmittances $T'(K_1)$ shown in FIGS. 17A and 17B. Referring to FIG. 18, without modification of an angle of incidence shown in FIG. 17A, a film thickness is maximized at position-direction pixel number j=600 at which angle of incidence $\theta_0$ is zero, and a film thickness decreases toward opposing ends because of increase in angle of incidence $\theta_0$.

In contrast, it can be seen that, with modification of an angle of incidence shown in FIG. 17B, 10 [μm] which is a proper film thickness is correctly calculated at all position-direction pixel numbers j.

As set forth above, by adopting the theoretical formula according to the present embodiment, physical characteristics in consideration of angle of incidence $\theta_0$ corresponding to a measurement point can accurately be reproduced. Accurate fitting can be achieved by using the formulae as above.

(e4: Processing Procedure (No. 2) in Film Thickness Measurement Method)

In the processing procedure (No. 1) in the film thickness measurement method described above, a method of calculating a film thickness by subjecting wave number distribution characteristics calculated from two-dimensional image 150 subjected to measurement by introducing wave number $K_1$ to Fourier transform is exemplified. A method of calculating a film thickness by fitting between a theoretically generated two-dimensional image and two-dimensional image 150 subjected to measurement instead of such a method will be described.

Figure 19:
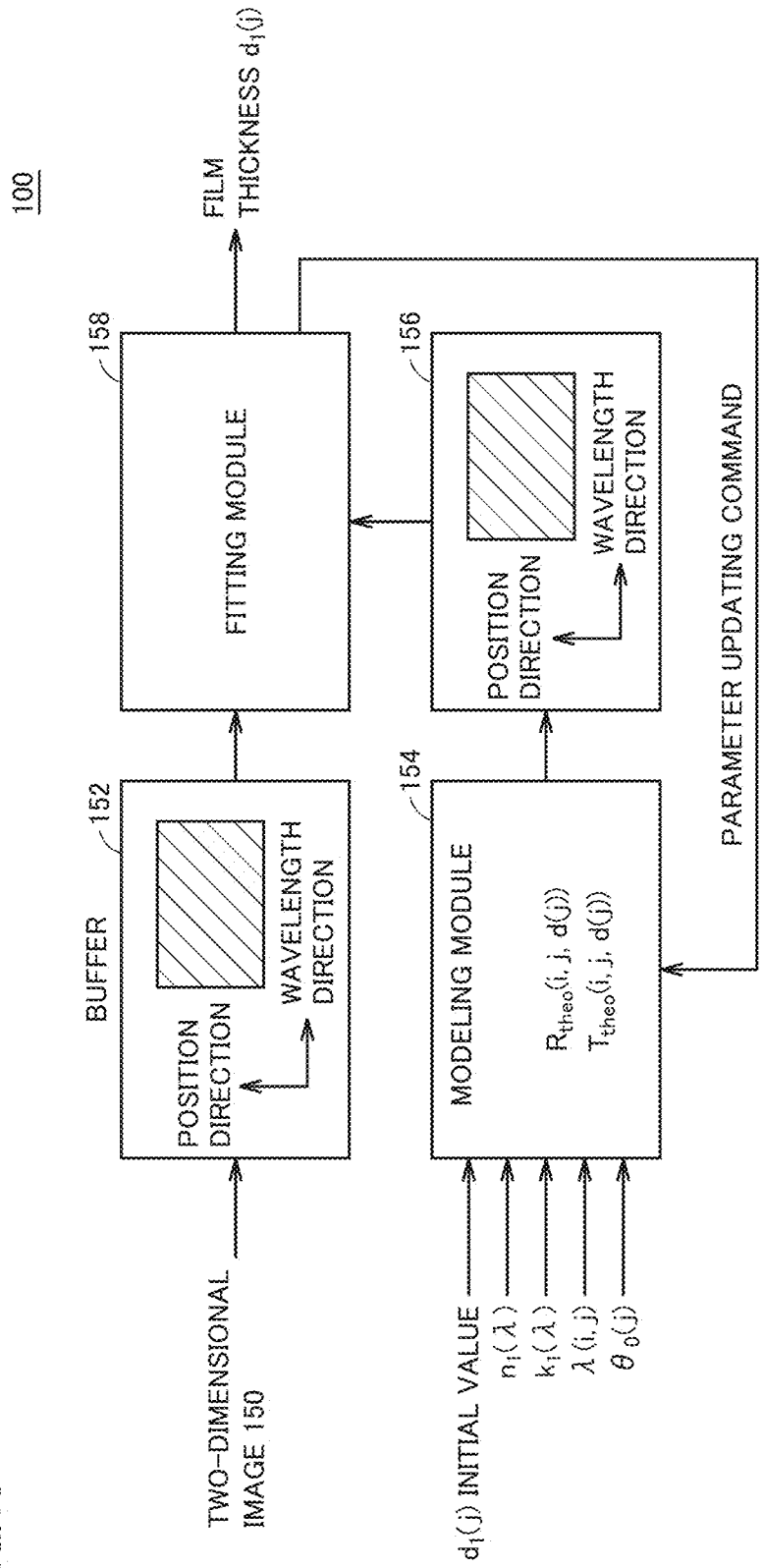
FIG. 19 is a schematic diagram for illustrating processing contents in a processing procedure (No. 2) in the film thickness measurement method according to the present embodiment.

FIG. 19 is a schematic diagram for illustrating processing contents in a processing procedure (No. 2) in the film thickness measurement method according to the present embodiment. Each element shown in FIG. 19 is typically implemented by execution of measurement program 114 by processor 102 of processing device 100.

Referring to FIG. 19, processing device 100 includes buffers 152 and 156, a modeling module 154, and a fitting module 158. In the configuration shown in FIG. 19, modeling module 154 calculates a theoretical value of transmittance spectrum $T(\lambda)$ (or reflectance spectrum $R(\lambda)$) and adjusts film thickness $d_1$ defining a theoretical value such that correlation with an actually measured value of obtained transmittance spectrum $T(\lambda)$ (or reflectance spectrum $R(\lambda)$) is higher. Finally, a film thickness which leads to transmittance spectrum $T(\lambda)$ (or reflectance spectrum $R(\lambda)$) highest in correlation with the actually measured value of transmittance spectrum $T(\lambda)$ (or reflectance spectrum $R(\lambda)$) is output as a measurement result.

For the sake of convenience of description, a suffix "$_{meas}$" is attached to an m actually measured value of a transmittance spectrum or a reflectance spectrum and a suffix "$_{theo}$" is attached to a theoretical value of a transmittance spectrum or a reflectance spectrum.

More specifically, buffer 152 stores two-dimensional image 150 (actually measured value) imaged by measurement optical system 10. Buffer 156 stores a two-dimensional image (theoretical value) generated by modeling module 154. Fitting module 158 calculates a similarity by shape comparison (fitting) between two-dimensional image 150 (actually measured value) stored in buffer 152 and the two-dimensional image (theoretical value) stored in buffer 156, and outputs a parameter updating command to modeling module 154 so as to maximize the calculated similarity. An example in which a correlation value or a correlation matrix is used as a similarity is exemplified.

When the calculated similarity is equal to or greater than a predetermined threshold value, fitting module 158 outputs film thickness $d_1(j)$ at that time as a measurement result.

An initial value of film thickness $d_1(j)$, an optical constant in consideration of a wavelength dispersion of sample S (refractive index $n_1(\lambda)$ and an extinction coefficient $k_1(\lambda)$), wavelength conversion formula $\lambda(i, j)$ determined by wavelength calibration of measurement optical system 10, and angle of incidence $\theta_0(j)$ at each measurement point on measurement line 24 are input to modeling module 154. Modeling module 154 calculates a transmittance distribution $T_{theo}(i, j, d_1(j))$ or a reflectance distribution $R_{theo}(i, j, d_1(j))$ for pixel position (i, j) and film thickness $d_1(j)$ based on the input information. Modeling module 154 updates as appropriate film thickness $d_1(j)$ in accordance with a parameter updating command from fitting module 158. Reference is to be made to a formula (20) which will be described later for details of transmittance distribution $T_{theo}$ or reflectance distribution $R_{theo}$.

A wavelength distribution of a refractive index of the polyethylene thin film actually measured with a thickness monitor based on microscopic spectrophotometry as shown in FIG. 13 described above was adopted for refractive index $n_1$. By way of example, the Cauchy dispersion formula as shown in the formula (11) above is used for refractive index $n_1(\lambda)$ shown in FIG. 13.

In the example shown in FIG. 13, coefficients are set as $C_0=1.533731$, $C_1=429.0333$, and $C_2=2.09247\times10^8$.

Figure 20:
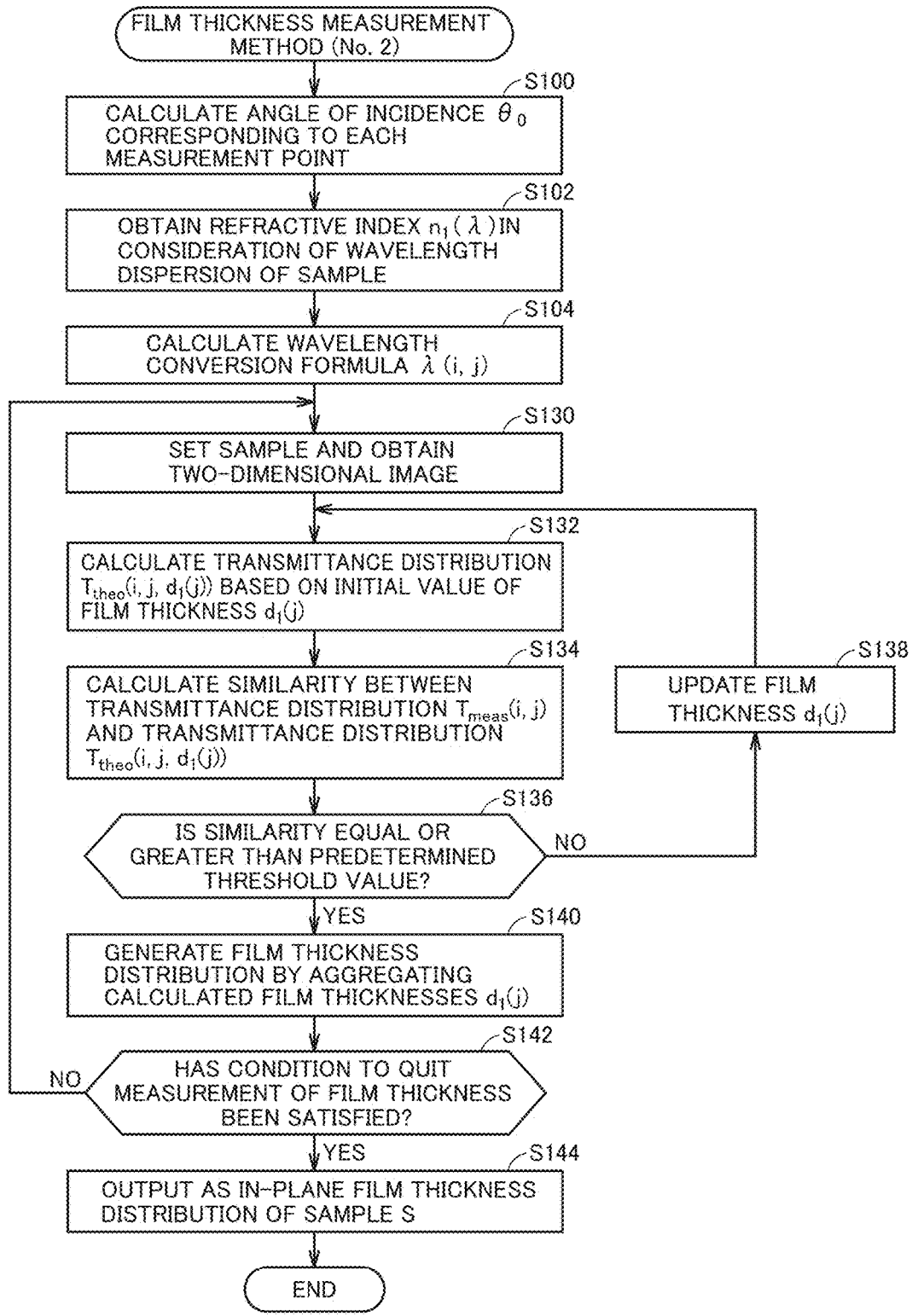
FIG. 20 is a flowchart showing the processing procedure (No. 2) in the film thickness measurement method according to the present embodiment.

FIG. 20 is a flowchart showing the processing procedure (No. 2) in the film thickness measurement method according to the present embodiment. Referring to FIG. 20, initially, processing device 100 calculates angle of incidence $\theta_0$ corresponding to each measurement point, of measurement interference light incident on measurement optical system 10 (step S100). A value representing magnitude of an angle of incidence corresponding to each measurement point is employed as a modification factor depending on an angle of incidence on the measurement optical system from each measurement point.

Then, processing device 100 obtains refractive index $n_1(\lambda)$ in consideration of a wavelength dispersion of sample S from a result of measurement for sample S with a measurement apparatus capable of optical constant analysis (for example, a thickness monitor based on microscopic spectrophotometry) (step S102). In succession, processing device 100 calculates wavelength conversion formula λ(i, j) representing relation between a pixel position in two-dimensional image 150 and wavelength λ based on a result of wavelength calibration for measurement optical system 10 (step S104).

Since the processing in steps S100 to S104 is the same as in steps S100 to S104 in the flowchart of the processing procedure (No. 1) in the film thickness measurement method shown in FIG. 11, detailed description will not be repeated. The processing in steps S100 to S104 above corresponds to a preparation step.

Sample S is set in optical measurement apparatus 1, and processing device 100 obtains two-dimensional image 150 imaged while sample S is irradiated with measurement light (step S130). Processing device 100 obtains transmittance distribution $T_{meas}(i, j)$ (or reflectance distribution $R_{meas}(i, j)$).

Processing device 100 calculates transmittance distribution $T_{theo}(i, j, d_1(j))$ (or reflectance distribution $R_{theo}(i, j, d_1(j))$) based on information calculated in steps S100 to S104 and the initial value of film thickness $d_1(j)$ (step S132). Processing device 100 adopts film thickness $d_1(j)$ at each measurement point as a fluctuating parameter and calculates a theoretical value of each pixel corresponding to two-dimensional image 150 based on refractive index $n_1$ of sample S, a value in accordance with magnitude of an angle of incidence corresponding to each measurement point, and correspondence between each measurement point and pixel position (i, j) in the two-dimensional image.

In succession, processing device 100 calculates a similarity between transmittance distribution $T_{meas}(i, j)$ (or reflectance distribution $R_{meas}(i, j)$) obtained in step S130 and transmittance distribution $T_{theo}(i, j, d_1(j))$ (or reflectance distribution $R_{theo}(i, j, d_1(j))$) calculated in step S132 by shape comparison therebetween (step S134).

More specifically, processing device 100 calculates a correlation matrix or a correlation coefficient between transmittance distribution $T_{meas}(i, j)$ (or reflectance distribution $R_{meas}(i, j)$) and transmittance distribution $T_{theo}(i, j, d_1(j))$ (or reflectance distribution $R_{theo}(i, j, d_1(j))$). A similarity for each position-direction pixel number j can be calculated by using the correlation matrix. When variation in film thickness $d_1(j)$ in the position direction is estimated to sufficiently be small, the film thickness may be regarded as $d_1(j)=d_1$ and a one-dimensional value (that is, a correlation value) which is summarization of the entire spectra may be calculated.

Processing device 100 determines whether or not the similarity calculated in step S134 is equal to or greater than a predetermined threshold value (step S136). When the calculated similarity is smaller than the predetermined threshold value (NO in step S136), processing device 100 updates film thickness $d_1(j)$ (step S138) and repeats processing in step S132 or later. Film thickness $d_1(j)$ may be updated for each position-direction pixel number j in accordance with magnitude of a corresponding similarity, or a prescribed amount may be added or subtracted in common.

When the calculated similarity is equal to or greater than the predetermined threshold value (YES in step S136), processing device 100 aggregates current film thicknesses $d_1(j)$ and outputs the resultant aggregate as a film thickness distribution on measurement line 24 of sample S (step S140).

Thus, processing device 100 determines a film thickness at each measurement point by adjusting a fluctuating parameter such that a similarity between a calculated theoretical value of each pixel and each pixel value of two-dimensional image 150 is higher. The fluctuating parameter is adjusted such that correlation close to similitude relation is found between the calculated theoretical waveform and an actually measured waveform.

In succession, processing device 100 determines whether or not a condition to quit measurement of a film thickness for sample S has been satisfied (step S142). When the condition to quit measurement of a film thickness for sample S has not been satisfied (NO in step S142), processing device 100 repeats the processing in step S130 or later.

In contrast, when the condition to quit measurement of a film thickness for sample S has been satisfied (YES in step S142), processing device 100 integrates the film thickness distributions successively calculated in step S140 and outputs the resultant film thickness distribution as a film thickness distribution (an in-plane film thickness distribution) at the measurement surface of sample S (step S144). Then, the process ends.

As set forth above, in the processing procedure (No. 2) in the film thickness measurement method, a film thickness (or a film thickness distribution) of sample S is determined by shape comparison (fitting) between an actually measured value of a transmittance spectrum or a reflectance spectrum representing wavelength distribution characteristics obtained from sample S and a theoretical value of a transmittance spectrum or a reflectance spectrum determined in accordance with a model formula (theoretical formula) having angle of incidence $\theta_0$, refractive index $n_1(\lambda)$, wavelength λ, and film thickness $d_1(j)$ as parameters.

More specifically, a correlation matrix (or a correlation value) with transmittance distribution $T_{meas}(i, j)$ (or reflectance distribution $R_{meas}(i, j)$) is calculated with film thickness $d_1(j)$ being varied in transmittance distribution $T_{theo}(i, j, d_1(j))$ (or reflectance distribution $R_{theo}(i, j, d_1(j))$), and film thickness $d_1(j)$ highest in correlation (that is, having a correlation coefficient closest to one) is output as a final result.

A film thickness distribution (an in-plane film thickness distribution) of sample S can be measured through the process as above.

In the processing procedure (No. 2) in the film thickness measurement method described above, though description has been given with attention being paid to transmittance distribution $T_{theo}(i, j, d_1(j))$ or reflectance distribution $R_{theo}(i, j, d_1(j))$ calculated in consideration of angle of incidence $\theta_0$ as a modification factor depending on angle of incidence $\theta_0$ on measurement optical system 10 from a measurement point, the modification factor is not limited thereto. For example, the modification factor is a concept which may encompass wave number $K_1$ described above.

In steps S136 and S138 described above, a range and a pitch of film thickness parameter $d_1(j)$ to be varied are set for transmittance distribution $T_{theo}(i, j, d_1(j))$ (or reflectance distribution $R_{theo}(i, j, d_1(j))$), and transmittance distribution $T_{theo}(i, j, d_1(j))$ (or reflectance distribution $R_{theo}(i, j, d_1(j))$) for film thickness value $d_1(j)$ within the set range of variation is calculated in advance. Then, a correlation matrix or a correlation coefficient between transmittance distribution $T_{theo}(i, j, d_1(j))$ (or reflectance distribution $R_{theo}(i, j, d_1(j))$) calculated in advance and actually measured transmittance distribution $T_{theo}(i, j)$ (or reflectance distribution $R_{theo}(i, j)$) may be calculated in a round-robin fashion, and film thickness value $d_1(j)$ at which a similarity (a correlation coefficient) is highest in a result of calculation may be determined as a film thickness at each measurement point.

(e5: Multi-Layered Film Sample)

Though processing for measuring a thickness of one layer has mainly been described for the sake of convenience of description, limitation thereto is not intended and a thickness of each layer in a multi-layered film sample can be measured. A refractive index of each layer in the multi-layered film sample can also be measured.

In measuring a thickness of each layer of the multi-layered film sample in the processing procedure (No. 1) in the film thickness measurement method described above, a plurality of peaks in accordance with thicknesses of layers appear in power spectrum $P(K_1)$ obtained through Fourier transform of wave-number-converted transmittance T' or wave-number-converted reflectance R'. A thickness of each layer forming a sample of interest can be calculated by analyzing the plurality of peaks which appear in power spectrum $P(K_1)$.

In measuring a thickness of each layer of the multi-layered film sample in the processing procedure (No. 2) in the film thickness measurement method, a thickness of each layer forming a sample of interest can be calculated by performing fitting for each layer by using a model formula including an optical constant (a refractive index and an extinction coefficient) of each layer in consideration of a wavelength dispersion and a thickness of each layer.

(e6: In-Line Measurement/Off-Line Measurement)

Though a processing example in which a film thickness is measured in succession to imaging of a two-dimensional image of sample S is mainly shown in the description above, limitation to such in-line measurement or real-time measurement is not intended, and for example, two-dimensional images of sample S may successively be imaged and a film thickness trend (an in-plane film thickness distribution) may subsequently be output.

F. Refractive Index Measurement Method

Though refractive index $n_1(\lambda)$ of sample S is measured in advance with a thickness monitor based on microscopic spectrophotometry in the film thickness measurement method described above, refractive index $n_1(\lambda)$ of sample S can also be measured with the optical measurement apparatus according to the present embodiment.

(f1: Overview)

Initially, a small piece of identical sample S (for example, of a 1-mm square) is arranged at each measurement point on the measurement line and actually measured values (transmittance distribution $T_{meas}(i, j)$ or reflectance distribution $R_{meas}(i, j)$) at the measurement points are successively obtained. Namely, a transmittance spectrum or a reflectance spectrum in the wavelength direction (that is, a distribution of actually measured values) when position-direction pixel number j (that is, angle of incidence $\theta_0$) is different for the same sample S is determined.

Unknown refractive index $n_1(\lambda)$ is determined by applying such advance information as film thickness $d_1$ being the same to transmittance distribution $T_{meas}(i, j)$ (or reflectance distribution $R_{meas}(i, j)$) measured for the same sample S.

Figure 21:
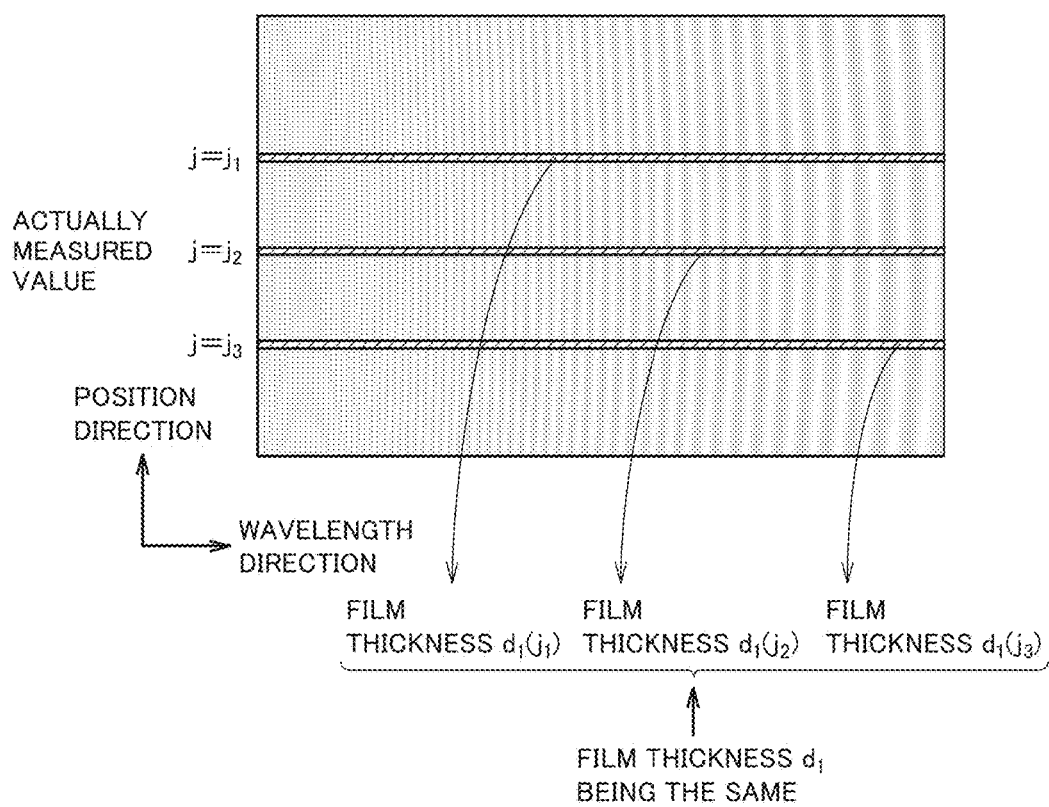
FIGS. 21 and 22 are schematic diagrams for illustrating overview of a refractive index measurement method according to the present embodiment.
Figure 22:
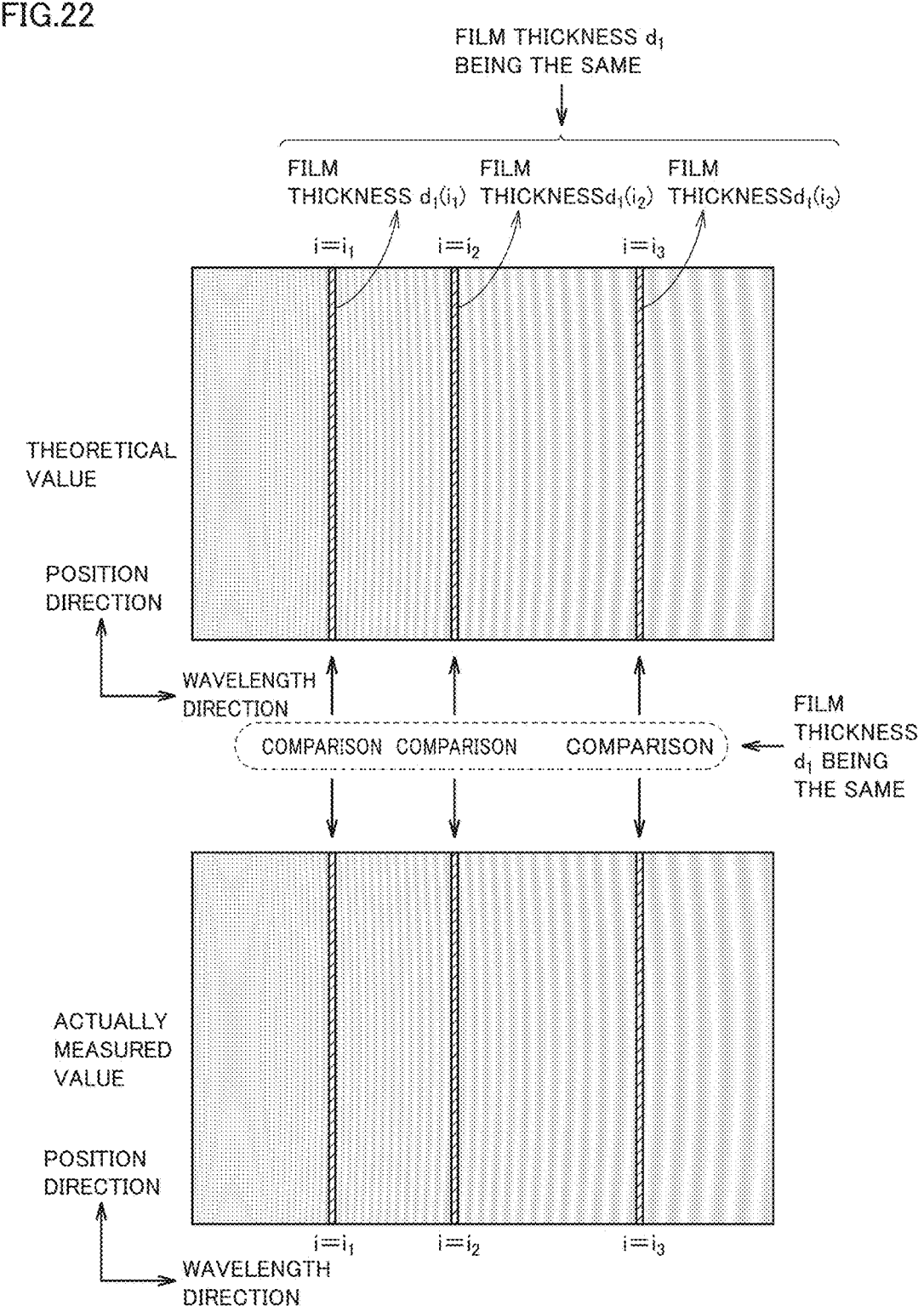

FIGS. 21 and 22 are schematic diagrams for illustrating overview of the refractive index measurement method according to the present embodiment. FIG. 21 shows an example in which refractive index $n_1(\lambda)$ of sample S is measured by using an intensity distribution at specific position-direction pixel number j. FIG. 22 shows an example in which refractive index $n_1(\lambda)$ of sample S is measured by using an intensity distribution at specific wavelength-direction pixel number i.

Referring to FIG. 21, with attention being paid to position-direction pixel number j, refractive index $n_1(\lambda)$ of sample S is set to a provisional value and then film thickness $d_1(j)$ ($j_1$, $j_2$, $j_3$, . . . ) is calculated from transmittance distribution $T_{meas}(i, j)$ (or reflectance distribution $R_{meas}(i, j)$) at specific position-direction pixel number j. Since film thickness $d_1$ is the same, refractive index $n_1(\lambda)$ of sample S is determined such that calculated film thicknesses $d_1(j)$ are consistent.

Referring to FIG. 22, with attention being paid to specific wavelength-direction pixel number i, unknown refractive index $n_1(\lambda)$ is determined by applying such advance information as film thickness $d_1$ being the same to a difference between a theoretical value and an actually measured value.

More specifically, initially, transmittance distribution $T_{theo}(i, j, d_1, n_1(i))$ (or reflectance distribution $R_{theo}(i, j, d_1, n_1(i))$) is compared with transmittance distribution $T_{meas}(i, j)$ (or reflectance distribution $R_{meas}(i, j)$) at corresponding position-direction pixel number j.

Transmittance distribution $T_{theo}$ (or reflectance distribution $R_{theo}$) takes a value dependent on pixel position (i, j), film thickness $d_1$, and refractive index $n_1(\lambda)$. Pixel position (i, j) has already been known and film thickness $d_1$ is the same regardless of wavelength-direction pixel number i. Therefore, refractive index $n_1(\lambda)$ can be determined by applying such advance information as film thickness $d_1$ being the same to a result of comparison between the theoretical value and the actually measured value for a plurality of wavelength-direction pixel numbers i (i=$i_1$, $i_2$, $i_3$, . . . ).

Referring to FIG. 22, with attention being paid to specific wavelength-direction pixel number i as in an example in which attention is paid to position-direction pixel number j, refractive index $n_1(\lambda)$ of sample S is set to a provisional value and then film thickness $d_1(i)$ (i=$i_1$, $i_2$, $i_3$, . . . ) is calculated from transmittance distribution $T_{meas}(i,j)$ (or reflectance distribution $R_{meas}(i, j)$) at specific wavelength-direction pixel number i. Since film thickness $d_1$ is the same, refractive index $n_1(\lambda)$ of sample S is determined such that calculated film thicknesses $d_1(j)$ are consistent.

According to the refractive index measurement method according to the present embodiment, refractive index $n_1$ of sample S can be measured with the optical measurement apparatus according to the present embodiment without using a dedicated measurement apparatus such as a thickness monitor based on microscopic spectrophotometry.

For example, a film thickness trend is obtained by setting any refractive index $n_1$ to any initial value (for example, 1 for all wavelengths) in accordance with operational processing with a function to correct angle of incidence $\theta_0$ as described above and varying a position to arrange a small piece of sample S. When a set value of refractive index $n_1$ is different from an actual refractive index of sample S, the film thickness trend does not become flat. By varying as appropriate refractive index $n_1$ with a least squares method, such a refractive index $n_1$ as achieving the flattest film thickness trend, that is, minimizing a film thickness dispersion, can be determined.

Refractive index $n_1$ may be found as a constant on average for all wavelengths, or when more strict calculation of the refractive index is desired, for example, the Cauchy dispersion formula $n_1(\lambda)=E+(F/\lambda^2)+(G/\lambda^4)$ is assumed in consideration of a wavelength dispersion, and a coefficient in each term may be found with the least squares method.

Alternatively, a refractive index may be calculated with such a method as minimizing a squared residual value of a film thickness with attention being paid to a specific line relatively large in angle of incidence.

In the refractive index measurement method described above, film thicknesses $d_1(i)$ at a plurality of positions in a distribution of actually measured values are calculated based on set refractive index $n_1(\lambda)$, a modification factor corresponding to each position, and a group of pixel values in the wavelength direction at each position. A film thickness dispersion which is a dispersion for each calculated film thickness $d_1(i)$ is calculated. Then, processing for calculating film thickness $d_1(i)$ and processing for calculating a film thickness dispersion are repeated with a refractive index of sample S being set to a plurality of different values. Finally, a refractive index of sample S is determined based on the calculated film thickness dispersion.

In the present embodiment, a distribution of actually measured values corresponding to two-dimensional image 150 (transmittance distribution $T_{meas}(i, j)$ or reflectance distribution $R_{meas}(i, j)$) is obtained by successively arranging sample S to measurement points irradiated with measurement light and successively obtaining actually measured values at the measurement points. A modification factor depending on an angle of incidence on measurement optical system 10 from each measurement point (a value representing magnitude of an angle of incidence corresponding to each measurement point) is calculated in association with a region in two-dimensional image 150 corresponding to each measurement point in sample S irradiated with measurement light. Optical characteristics including a refractive index of sample S are calculated based on a group of pixel values in one row or a plurality of rows along any one direction in the distribution of the actually measured values and a corresponding modification factor. In the distribution of the actually measured values, such advance information as film thickness $d_1$ being the same is made use of.

Each case will be described below in further detail.

(f2: Refractive Index Measurement Method (No. 1) Based on Information in Wavelength Direction)

Initially, the refractive index measurement method (No. 1) based on information in the wavelength direction will be described. Initially, an example in which a condition of $n_1(\lambda)=n_1$ (constant value) is satisfied without taking wavelength-dependency of a refractive index of sample S into consideration will be described first.

In the refractive index measurement method (No. 1) based on the information in the wavelength direction, refractive index $n_1$ of sample S is set to some initial value and film thicknesses $d_1$ are calculated for a transmittance spectrum (or a reflectance spectrum) at a plurality of wavelength-direction pixel numbers i based on refractive index $n_1$. Then, a film thickness trend of a plurality of calculated film thicknesses $d_1$ is evaluated. Refractive index $n_1$ is fitted so as to flatten the film thickness trend. When actual refractive index $n_1$ of sample S is different from set refractive index $n_1$, the film thickness trend cannot maintain flatness. This is based on the premise that a film thickness at a fixed point in sample S should take a constant value in measurement at any angle of incidence $\theta_0$ by adopting a calculation method in consideration of influence by angle of incidence $\theta_0$ of measurement interference light as described above.

Flatness of the film thickness trend is adopted as a cost function based on such a premise, and refractive index $n_1$ which minimizes a value of the cost function is determined. A film thickness in measurement at the fixed point in sample S at position-direction pixel number j is denoted as $d_1(j)$. A film thickness trend curve $d_1(j)$ with position-direction pixel number j being varied is approximated to a constant function $f(j)=\mu$ ($\mu$ being a constant value). A sum of squared residuals S can be defined as in a formula (12) below. Constant value $\mu$ in the formula (12) is determined with the least squares method. More specifically, a formula (13) below is obtained by finding constant value $\mu$ under such a condition that sum of squared residuals S is minimized, that is, a condition of $\partial S/\partial \mu = 0$ is satisfied.

$$S = \sum_{j=1}^{C_y/B_y} \{d_1(j) - \mu\}^2 \qquad (12)$$

$$\mu = \frac{B_y}{C_y} \sum_{j=1}^{C_y/B_y} d_1(j) \equiv \overline{d_1} \qquad (13)$$

Constant value $\mu$ calculated in accordance with the formula (12) corresponds to an average value of film thicknesses $d_1(j)$. Since sum of squared residuals S is a sum of squared residuals of the average value of film thicknesses $d_1(j)$, it corresponds to a dispersion of film thicknesses $d_1(j)$ (which is referred to as a "film thickness dispersion" below).

Since a film thickness trend, an average value of film thicknesses, and a film thickness dispersion (a sum of squared residuals of a film thickness) are all dependent on refractive index $n_1$, film thickness dispersion $D(n_1)$ of film thickness $d_1(j)$ can be defined as a cost function as in a formula (14) below.

$$D(n_1) = \frac{B_y}{C_y} \sum_{j=1}^{C_y/B_y} \{d_1(n_1, j) - \overline{d_1}(n_1)\}^2 \qquad (14)$$

In the formula (14) above, refractive index $n_1$ under the condition that film thickness dispersion $D(n_1)$ is minimized, that is, a condition of $\partial D/\partial n_1 = 0$ is satisfied, can be found by sequentially varying a value of refractive index $n_1$.

Figure 23A:
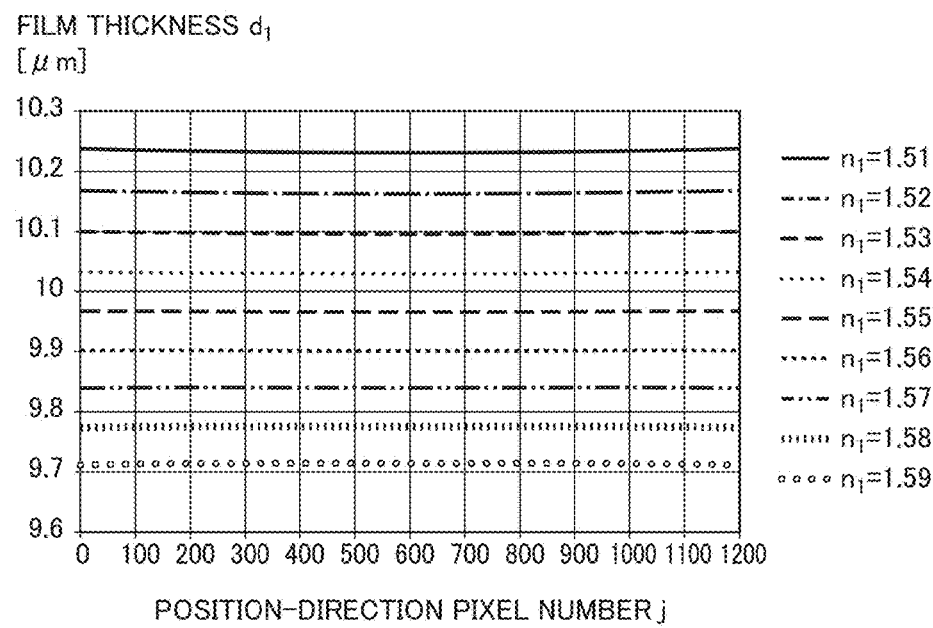
FIGS. 23A and 23B are graphs showing examples of a film thickness trend calculated in accordance with a refractive index measurement method (No. 1) based on information in a wavelength direction according to the present embodiment.
Figure 23B:
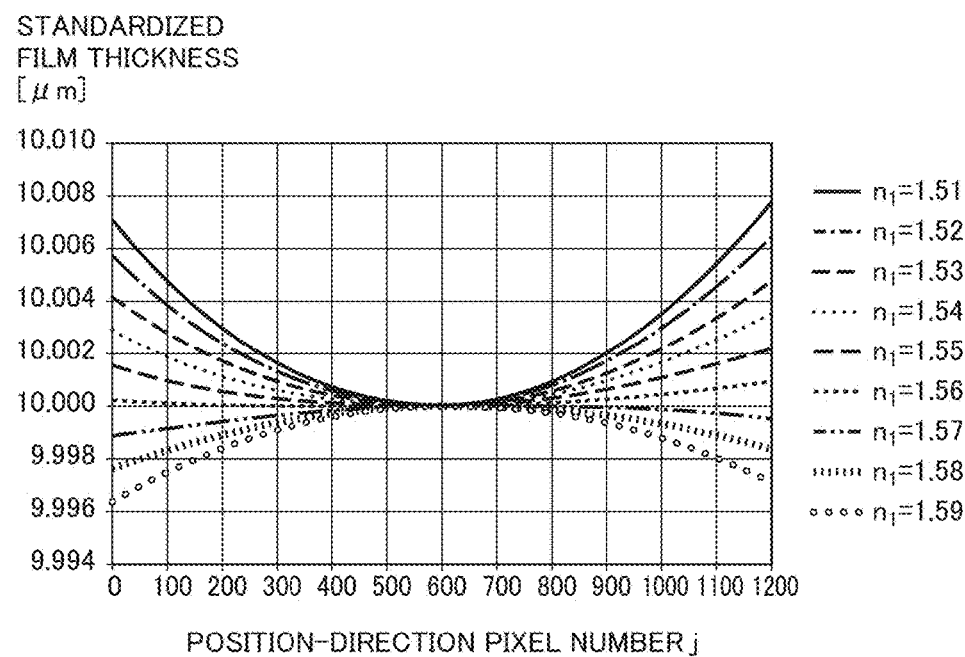

FIGS. 23A and 23B are graphs showing examples of film thickness trends calculated in accordance with the refractive index measurement method (No. 1) based on information in the wavelength direction according to the present embodiment. The graph in FIG. 23A shows the film thickness trend for each refractive index $n_1$ (constant value) of a polyethylene thin film. For facilitation of comparison of variation in film thickness trend, the graph in FIG. 23B shows a result of such standardization as achieving film thickness $d_1=10$ [μm] at position-direction pixel number j=600. In calculating the film thickness trends in FIGS. 23A and 23B, a theoretical value of transmittance spectrum $T(\lambda)$ used in generating the two-dimensional image shown in FIG. 15 described above was used.

It can be seen that, with increase in refractive index $n_1$ of sample S from 1.51 in increments of 0.01, the film thickness trend varies from downwardly projecting to upwardly projecting since increase from 1.56 to 1.57. It can be seen that, when refractive index $n_1$ is set to 1.56, film thickness dispersion $D(n_1)$ is minimized and the film thickness trend is also flattest. Table 1 below shows values involved with the film thickness trends shown in FIGS. 23A and 23B.

TABLE 1

| Refractive Index $n_1$ | Average Value of Film Thickness $\overline{d1}$ ($n_1$) | Film Thickness Dispersion D ($n_1$) |
|---|---|---|
| 1.51 | 10.232 | $5.072 \times 10^{-6}$ |
| 1.52 | 10.165 | $3.271 \times 10^{-6}$ |
| 1.53 | 10.098 | $1.815 \times 10^{-6}$ |
| 1.54 | 10.031 | $9.265 \times 10^{-7}$ |
| 1.55 | 9.967 | $3.240 \times 10^{-7}$ |
| 1.56 | 9.902 | $5.609 \times 10^{-8}$ |
| 1.57 | 9.838 | $9.641 \times 10^{-8}$ |
| 1.58 | 9.776 | $3.981 \times 10^{-7}$ |
| 1.59 | 9.714 | $9.365 \times 10^{-7}$ |

When refractive index $n_1$ is calculated with accuracy of 1/100 from results of calculation as above, refractive index $n_1$ can be determined as 1.56.

Though the formulae (12), (13), and (14) above are written to use all of position-direction pixel numbers j in calculation of film thickness dispersion $D(n_1)$, all of them do not necessarily have to be used, and a prescribed number of pixel rows may be used in accordance with required accuracy. In this case, measurement points at which sample S is arranged should also be arranged at intervals greater than a resolution in the film thickness measurement method.

Figure 24:
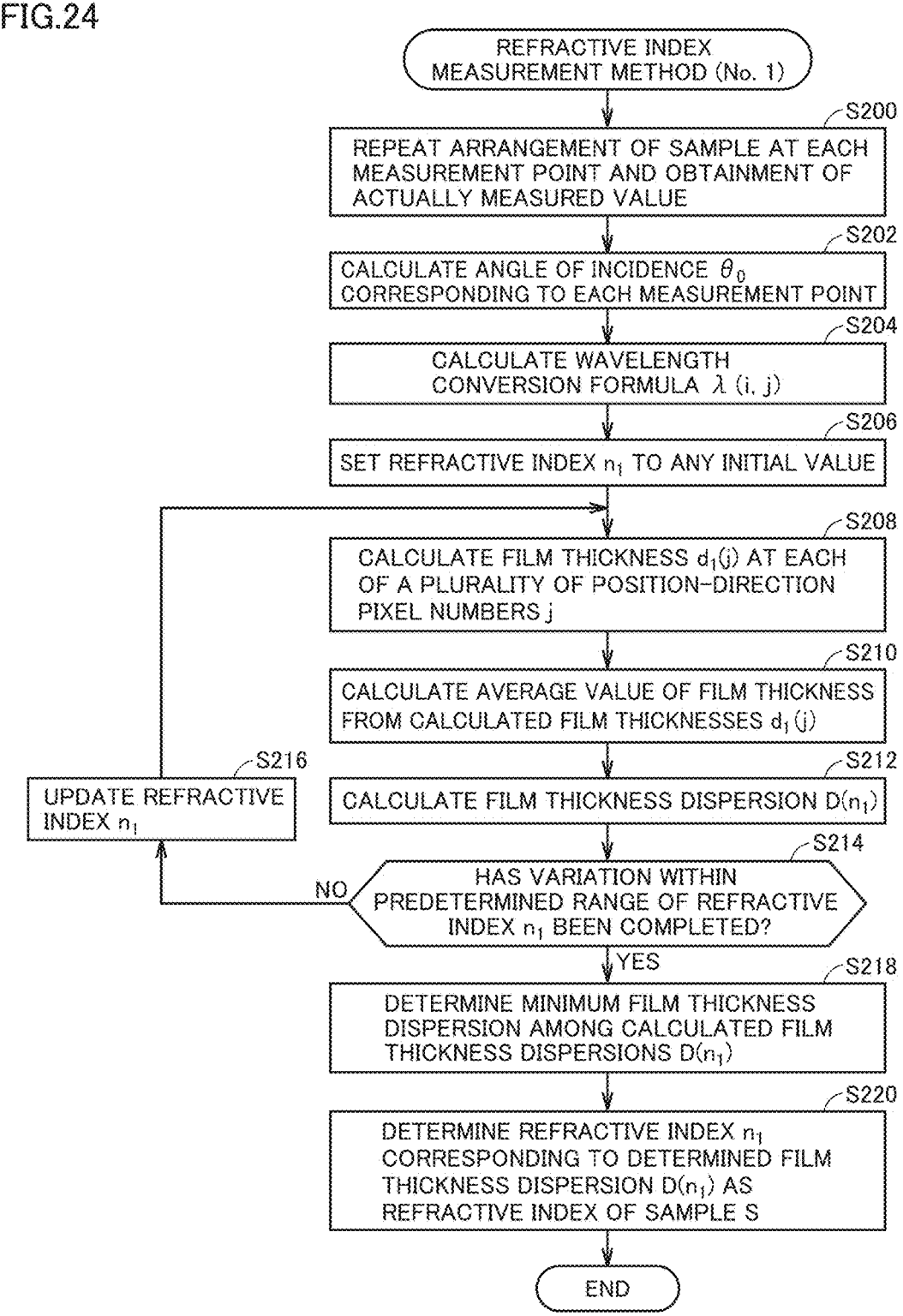
FIG. 24 is a flowchart showing a processing procedure in the refractive index measurement method (No. 1) based on information in the wavelength direction according to the present embodiment.

FIG. 24 is a flowchart showing a processing procedure in the refractive index measurement method (No. 1) based on information in the wavelength direction according to the present embodiment. Referring to FIG. 24, initially, a user repeats arrangement of a small piece of sample S at each measurement point on the measurement line and obtainment of an actually measured value from arranged sample S by operating optical measurement apparatus 1 (step S200). Processing device 100 thus obtains transmittance distribution $T_{meas}(i, j)$ (or reflectance distribution $R_{meas}(i, j)$) measured for the same sample S.

In succession, processing device 100 calculates angle of incidence $\theta_0$ corresponding to each measurement point, of measurement interference light incident on measurement optical system 10 (step S202). Then, processing device 100 calculates wavelength conversion formula $\lambda(i, j)$ representing relation between a pixel position in two-dimensional image 150 and wavelength $\lambda$ from a result of wavelength calibration for measurement optical system 10 (step S204).

Since processing in steps S202 and S204 is the same as in steps S100 and S104 in the flowchart of the processing procedure (No. 1) in the film thickness measurement method shown in FIG. 11, detailed description will not be repeated.

In succession, processing device 100 sets refractive index $n_1$ to any initial value (step S206). Then, processing device 100 calculates film thicknesses $d_1(j)$ from transmittance distribution $T_{meas}(i, j)$ (or reflectance distribution $R_{meas}(i, j)$) at a plurality of position-direction pixel numbers j (step S208).

Processing device 100 calculates an average value of calculated film thicknesses $d_1(j)$ (step S210) and calculates film thickness dispersion $D(n_1)$ by using the average value of the film thicknesses calculated in step S210 (step S212). Processing device 100 then determines whether or not variation in refractive index $n_1$ within a predetermined range has been completed (step S214). When variation in refractive index $n_1$ within the predetermined range has not been completed (NO in step S214), processing device 100 updates refractive index $n_1$ (step S216) and repeats processing in step S208 or later.

When variation in refractive index $n_1$ within the predetermined range has been completed (YES in step S214), processing device 100 determines a minimum film thickness dispersion of film thickness dispersions $D(n_1)$ calculated in step S212 (step S218) and determines refractive index $n_1$ corresponding to determined film thickness dispersion $D(n_1)$ as a refractive index of sample S (step S220). Then, the process ends. Refractive index $n_1$ at which calculated film thickness dispersion $D(n_1)$ becomes small is determined as a refractive index of sample S.

Refractive index $n_1$ of sample S can be determined based on the information in the wavelength direction as above.

(f3: Refractive Index Measurement Method (No. 2) Based on Information in Wavelength Direction)

Though a method of analytically determining refractive index $n_1$ of sample S is exemplified in the refractive index measurement method (No. 1) based on the information in the wavelength direction described above, refractive index $n_1$ may be determined by fitting by using a predetermined polynomial.

Figure 25:
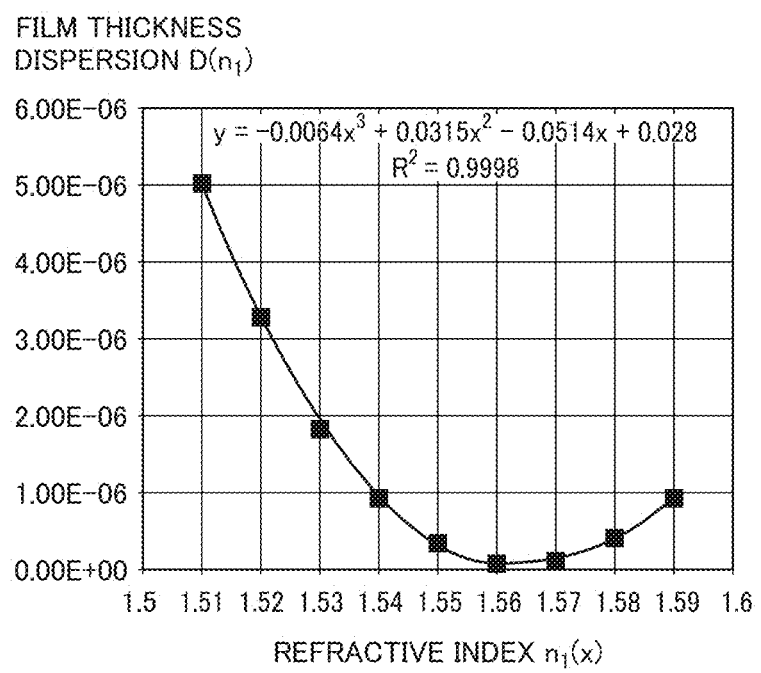
FIG. 25 is a diagram for illustrating a method of determining a refractive index in the refractive index measurement method (No. 2) based on information in the wavelength direction according to the present embodiment.

FIG. 25 is a diagram for illustrating a method of determining refractive index $n_1$ in the refractive index measurement method (No. 2) based on the information in the wavelength direction according to the present embodiment. FIG. 25 shows a graph in which film thickness dispersion $D(n_1)$ calculated at the time of variation in refractive index $n_1$ is plotted. For example, a cubic polynomial as shown in a formula (15) below can be fitted to relation between refractive index $n_1$ and film thickness dispersion $D(n_1)$ as shown in FIG. 25.

Coefficients $A_3$, $A_2$, $A_1$, and $A_0$ in the formula (15) are fitted to pass through film thickness dispersion $D(n_1)$ shown in FIG. 25. Refractive index $n_1$ can be determined in correspondence with a point where the cubic polynomial fitted as shown in FIG. 25 takes a relative minimum value (a minimum value). Refractive index $n_1$ can be calculated based on coefficients $A_3$, $A_2$, $A_1$, and $A_0$ in accordance with a formula (16) below.

$$D = A_3 x^3 + A_2 x^2 + A_1 x + A_0 \tag{15}$$

$$n_1 = \frac{-A_2 + \sqrt{A_2^2 - 3 A_3 A_1}}{3 A_3} \tag{16}$$

Table 2 below shows results obtained by fitting shown in FIG. 25.

TABLE 2

| $D = A_3 x^3 + A_2 x^2 + A_1 x^1 + A_0$ | | | | |
|---|---|---|---|---|
| $A_3$ | $A_2$ | $A_1$ | $A_0$ | Refractive Index $n_1$ |
| −0.006408 | 0.031479 | −0.051442 | 0.027969 | 1.5634 |

When refractive index $n_1$ is calculated with accuracy of 1/10000 from results of calculation as above, refractive index $n_1$ can be determined as 1.5634. A refractive index can be determined with accuracy higher than variation in refractive index $n_1$ (in this example, in increments of 0.01 (that is, accuracy of 1/100)).

A refractive index of sample S can be determined by fitting a polynomial representing a predetermined film thickness dispersion to relation between a refractive index and a film thickness dispersion, based on a point at which the film thickness dispersion represented by the polynomial determined by fitting takes an extreme value.

In the processing procedure in the refractive index measurement method (No. 2) based on the information in the wavelength direction, fitting with the polynomial as shown in FIG. 25 is performed instead of steps S218 and S220 in the flowchart shown in FIG. 24. Since the processing procedure is otherwise the same as in the refractive index measurement method (No. 1) based on the information in the wavelength direction described above, detailed description will not be repeated.

(f4: Refractive Index Measurement Method (No. 3) Based on Information in Wavelength Direction)

Refractive index $n_1$ of sample S can more efficiently be determined by paying attention to information affected more by angle of incidence $\theta_0$ of the information in the wavelength direction as described above. More specifically, initially, a squared residual value $y(n_1, j)$ representing a deviation from an average value of film thicknesses $d_1(j)$ at any position-direction pixel number j is defined as shown in a formula (17) below.

$$y(n_1, j) = \{d_1(n_1, j) - \overline{d}_1(n_1)\}^2 \quad (17)$$

Figure 26:
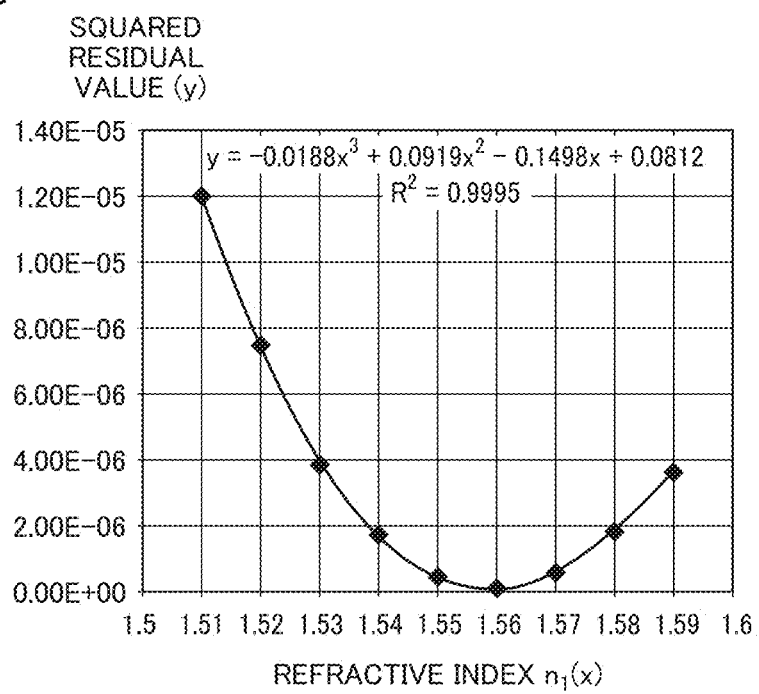
FIG. 26 is a diagram for illustrating a method of determining a refractive index in the refractive index measurement method (No. 3) based on information in the wavelength direction according to the present embodiment.

FIG. 26 is a diagram for illustrating a method of determining refractive index $n_1$ in the refractive index measurement method (No. 3) based on information in the wavelength direction according to the present embodiment. FIG. 26 shows a graph in which squared residual value y calculated at the time of variation in refractive index $n_1$ is plotted. For example, the cubic polynomial as shown in the formula (15) above can be fitted to relation between refractive index $n_1$ and squared residual value y as shown in FIG. 26.

Coefficients $A_3$, $A_2$, $A_1$, and $A_0$ in the formula (15) are fitted to pass through squared residual value y shown in FIG. 26. Refractive index $n_1$ can be determined in correspondence with a point where the cubic polynomial fitted as shown in FIG. 26 takes a relative minimum value (a minimum value). Refractive index $n_1$ can be calculated based on coefficients $A_3$, $A_2$, $A_1$, and $A_0$ in accordance with the formula (16) above.

Table 3 below shows results obtained by fitting shown in FIG. 26.

TABLE 3

$y = A_3 x^3 + A_2 x^2 + A_1 x^1 + A_0$

| j | $A_3$ | $A_2$ | $A_1$ | $A_0$ | Refractive Index $n_1$ |
|---|---|---|---|---|---|
| 50 | −0.018765 | 0.091930 | −0.149815 | 0.081228 | 1.5587 |
| 100 | −0.008182 | 0.040403 | −0.066308 | 0.036179 | 1.5570 |
| 1100 | −0.010970 | 0.053523 | −0.086941 | 0.047020 | 1.5690 |
| 1150 | −0.013067 | 0.065614 | −0.109397 | 0.060590 | 1.5694 |
| | | | | Average of $n_1$ | 1.5636 |

In the table above, refractive index $n_1$ was calculated at four position-direction pixel numbers (j=50, 100, 1100, 1150) where angle of incidence $\theta_0$ is expected to be relatively large.

In the refractive index measurement method (No. 3) based on the information in the wavelength direction according to the present embodiment, a spectrum should be measured by arranging sample S at least two measurement points. Therefore, time and efforts for measurement can be lessened and refractive index $n_1$ can be calculated in a simplified manner. Positions where a difference in angle of incidence is great are preferably selected as measurement points where sample S is to be arranged.

Refractive index $n_1$ can also be calculated from a point where squared residual value y takes a relative minimum value (minimum value) with attention being paid to specific position-direction pixel number j where an angle of incidence is as large as possible. For example, when refractive index $n_1$ is calculated with accuracy of 1/10000 at position-direction pixel number j=50 in the table above, refractive index $n_1$ can be determined as 1.5587. By using a polynomial for fitting, a refractive index can be determined with accuracy higher than variation in refractive index $n_1$ (in this example, in increments of 0.01 (that is, accuracy of 1/100)).

A refractive index of sample S can be determined by thus fitting a polynomial representing a predetermined squared residual value to relation between refractive index $n_1$ and a squared residual value for each calculated film thickness, based on a point where the squared residual value expressed by the polynomial determined by fitting takes an extreme value.

The processing procedure in the refractive index measurement method (No. 3) based on the information in the wavelength direction is different from the processing procedure in the refractive index measurement method (No. 2) based on the information in the wavelength direction described above only in use of squared residual value y instead of film thickness dispersion $D(n_1)$. Since the processing procedure is otherwise the same as in the refractive index measurement method (No. 1) based on the information in the wavelength direction described above, detailed description will not be repeated.

(f5: Refractive Index Measurement Method (No. 4) Based on Information in Wavelength Direction)

In the description of the refractive index measurement method (No. 1) based on the information in the wavelength direction described above, a condition of refractive index $n_1(\lambda) = n_1$ (constant value) was assumed. In actual, however, refractive index $n_1(\lambda)$ is wavelength-dependent. In this case, refractive index $n_1(\lambda)$ is defined with a high-order formula and each coefficient in the high-order formula is to be fitted, so that refractive index $n_1(\lambda)$ in consideration of wavelength-dependency can be determined.

By way of example, a Cauchy dispersion formula as shown in a formula (18) below may be used. Coefficients (E, F, G) in terms in the formula (18) are varied, and a set of coefficients with which a value to be evaluated (film thickness dispersion $D(n_1)$ in the refractive index measurement method (No. 2) based on the information in the wavelength direction described above) takes a relative minimum value (a minimum value) should be determined with the least squares method.

In a formula (19) below in which film thickness dispersion D is dependent on coefficients (E, F, G), a set of coefficients (E, F, G) satisfying a condition of $\partial D/\partial E = \partial D/\partial F = \partial D/\partial G = 0$ is found, so that refractive index $n_1(\lambda)$ in consideration of wavelength-dependency can be found based on the formula (18).

$$n_1(\lambda) = E + \frac{F}{\lambda^2} + \frac{G}{\lambda^4} \quad (18)$$

$$D(E, F, G) = \frac{B_y}{C_y} \sum_{j=1}^{C_y/B_y} \{d_1(E, F, G, j) - \overline{d}_1(E, F, G)\}^2 \quad (19)$$

Though refractive index $n_1$ is calculated from a point where squared residual value y takes a relative minimum value (a minimum value) in the refractive index measurement method (No. 3) based on the information in the wavelength direction described above, refractive index $n_1(\lambda)$ in consideration of wavelength-dependency can be found also with this method. Refractive index $n_1(\lambda)$ in consideration of wavelength-dependency can be found from the formula (18) by deriving y(D, E, F) as in the formula (19) above and finding a set of coefficients (E, F, G) satisfying a condition of $\partial y/\partial E = \partial y/\partial F = \partial y/\partial G = 0$.

A refractive index of sample S can be determined by thus calculating a refractive index of sample S in accordance with a prescribed wavelength dispersion formula and applying the least squares method to any of relation between each coefficient defining the wavelength dispersion formula and a film thickness dispersion and relation between each coefficient defining the wavelength dispersion formula and the squared residual value, based on a set of coefficients at the time when the film thickness dispersion or the squared residual value takes an extreme value.

Refractive index $n_1(\lambda)$ in consideration of wavelength-dependency can be found in the procedure as above.

(f6: Refractive Index Measurement Method (No. 1) Based on Information in Position Direction)

The refractive index measurement method based on information in the position direction will now be described. As described with reference to FIG. 22 above, in measurement of refractive index $n_1$ of sample S based on information in the position direction, refractive index n(i) is determined by comparing a trend along position-direction pixel number j for one wavelength-direction pixel number i or a plurality of wavelength-direction pixel numbers i, in connection with transmittance distribution $T_{meas}(i, j)$ (or reflectance distribution $R_{meas}(i, j)$) measured for a small piece of the same sample S and transmittance distribution $T_{theo}(i, j, n_1(i))$ (or reflectance distribution $R_{theo}(i, j, n_1(i))$) calculated in accordance with a function including refractive index $n_1$.

Initially, for sample S (having film thickness $d_1$) of a thin film in air (medium 0) as shown in FIGS. 7A and 7B described above, transmittance distribution $T_{theo}$ in consideration of multiple reflection in sample S is as shown in a formula (20) below. Refractive index $n_0$ of air is defined as $n_0=1$.

$$T_{theo}(i, j, d_1, n_i(i)) = \frac{(1 - r_{01}^2)^2}{1 + r_{01}^4 - 2r_{01}^2 \cos\left\{\frac{4\pi d_1}{\lambda(i)}\sqrt{n_1(i)^2 - \sin^2\theta_0(j)}\right\}} \quad (20)$$

In the formula (20) above, amplitude reflectance $r_{01}$ is expressed as in a formula (21-1) below, for each of s polarization and p polarization. Since relation of $n_0 \cdot \sin\theta_0 = n_1 \cdot \sin\theta_1$ (Snell's law) is satisfied between angle of incidence $\theta_0$ and angle of refraction $\theta_1$, the formula (21-1) can be deformed as in a formula (21-2). Refractive index $n_0$ of air is defined as $n_0=1$. Amplitude reflectance $r_{01}$ can be defined only by refractive index $n_1$ of sample S and angle of incidence $\theta_0$.

$$\left.\begin{aligned}r_{01}^s &= \frac{n_0\cos\theta_0 - n_1\cos\theta_1}{n_0\cos\theta_0 + n_1\cos\theta_1}\\r_{01}^p &= \frac{n_1\cos\theta_0 - n_0\cos\theta_1}{n_1\cos\theta_0 + n_0\cos\theta_1}\end{aligned}\right\} \quad (21\text{-}1)$$

$$\left.\begin{aligned}r_{01}^s &= \frac{\cos\theta_0 - \sqrt{n_1^2 - \sin^2\theta_0}}{\cos\theta_0 + \sqrt{n_1^2 - \sin^2\theta_0}}\\r_{01}^p &= \frac{n_1^2\cos\theta_0 - \sqrt{n_1^2 - \sin^2\theta_0}}{n_1^2\cos\theta_0 + \sqrt{n_1^2 - \sin^2\theta_0}}\end{aligned}\right\} \quad (21\text{-}2)$$

Since an intensity reflectance $R_{01} = |r_{01}|^2$ when no polarization occurs includes components of both of s polarization and p polarization, definition as in a formula (22) below can be made.

$$|r_{01}|^2 = \frac{|r_{01}^s|^2 + |r_{01}^p|^2}{2} \quad (22)$$

By substituting the formula (21-1) and the formula (22) into the formula (20) above to cancel amplitude reflectance $r_{01}$, transmittance distribution $T_{theo}$ can be defined by refractive index $n_1(i)$ of sample S, angle of incidence $\theta_0(j)$, film thickness $d_1$ of sample S, and wavelength $\lambda(i)$.

As described above, transmittance distribution $T_{meas}(i, j)$ (or reflectance distribution $R_{meas}(i, j)$) is represented as a value measured by arranging a small piece of the same sample S at each measurement point on the measurement line, and film thickness $d_1$ takes a constant value without depending on wavelength-direction pixel number i and position-direction pixel number j.

With attention being paid to specific wavelength-direction pixel number i, a sum of squared residuals Q representing an error between transmittance distribution $T_{meas}(i, j)$ (or reflectance distribution $R_{meas}(i, j)$) and transmittance distribution $T_{meas}(i, j)$ (or reflectance distribution $R_{meas}(i, j)$) can be defined as in a formula (23) below.

$$Q(i, d_1, n_i(i)) = \frac{B_y}{C_y} \sum_{j=1}^{C_y/B_y} \{T_{theo}(i, j, d_1, n_1(i)) - T_{meas}(i, j)\}^2 \quad (23)$$

By satisfying a condition minimizing sum of squared residuals Q defined in the formula (23) above, that is, a condition of $\partial Q/\partial d_1 = \partial Q/\partial n_1(i) = 0$, refractive index $n_1(i)$ at wavelength-direction pixel number i of interest and corresponding film thickness $d_1$ can be determined.

Since film thickness $d_1$ takes a constant value without depending on wavelength-direction pixel number i and position-direction pixel number j, refractive index $n_1(i)$ calculated at one wavelength-direction pixel number i and corresponding film thickness $d_1$ may be output as final values when wavelength-dependency of refractive index $n_1$ is not taken into consideration (that is, when refractive index $n_1$ is constant).

In order to further enhance accuracy in measurement, a set of refractive index $n_1$ and film thickness $d_1$ may be determined for all wavelength-direction pixel numbers i. In this case, a result of statistical processing such as averaging of values of sets of refractive index $n_1$ and film thickness $d_1$ may finally be output.

As will be described in the refractive index measurement method (No. 3) based on the information in the position direction which will be described later, when wavelength-dependency of refractive index $n_1$ is taken into consideration, a plurality of wavelength-direction pixel numbers i should be considered.

Though the formula (23) above is written to use all of position-direction pixel numbers j in calculation of sum of squared residuals Q, all of them do not necessarily have to be used, and a prescribed number of pixel rows may be used in accordance with required accuracy. In this case, measurement points at which sample S is arranged should also be arranged at intervals greater than a resolution in the film thickness measurement method.

Since the processing procedure in the refractive index measurement method (No. 1) based on the information in the position direction is the same as the processing procedure in the refractive index measurement method (No. 1) based on the information in the wavelength direction shown in FIG. 24 except for a function of a sum of squared residuals, detailed description will not be repeated.

Thus, in the present measurement method, a distribution of actually measured values represented by a group of pixel values in the position direction for any wavelength in the distribution of the actually measured values is calculated, and a distribution of theoretical values for any wavelength is calculated based on a film thickness and a refractive index of a sample which are set in advance and a modification factor corresponding to each position. Then, a film thickness and a refractive index of the sample are determined so as to make an error between the distribution of the theoretical values and the distribution of the actually measured values smaller. A refractive index of the sample may be determined for each of a plurality of wavelengths in the distribution of the actually measured values.

(f7: Refractive Index Measurement Method (No. 2) Based on Information in Position Direction)

In the refractive index measurement method (No. 1) based on the information in the position direction described above, refractive index $n_1$ and film thickness $d_1$ are determined for each wavelength-direction pixel number i by comparing an actually measured value and a theoretical value with each other.

In the refractive index measurement method (No. 2) based on information in the position direction, refractive index $n_1$ is more highly accurately determined by applying such advance information as film thickness $d_1$ being the same. More specifically, a flatness of a film thickness trend may be adopted as a cost function, and refractive index $n_1$ at which a value of the cost function is minimized may be determined. A film thickness trend curve $d_1(i)$ at the time of variation in wavelength-direction pixel number i is approximated to a constant function $f(j)=\mu$ ($\mu$ being a constant value). A sum of squared residuals S can be defined as in a formula (24) below. Constant value $\mu$ in the formula (24) is determined with the least squares method. More specifically, a formula (25) below is obtained by finding constant value $\mu$ under such a condition that sum of squared residuals S is minimized, that is, a condition of $\partial S/\partial \mu = 0$ is satisfied.

$$S = \sum_{i=1}^{C_x/B_x} \{d_1(i) - \mu\}^2 \quad (24)$$

$$\mu = \frac{B_x}{C_x} \sum_{i=1}^{C_x/B_x} d_1(i) \equiv \overline{d_1} \quad (25)$$

Constant value $\mu$ calculated in accordance with the formula (25) corresponds to an average value of film thicknesses $d_1(i)$. Since sum of squared residuals S is a sum of squared residuals of the average value of film thicknesses $d_1(i)$, it corresponds to a dispersion of film thicknesses $d_1(i)$ (which is also referred to as a "film thickness dispersion" below).

Figure 27:
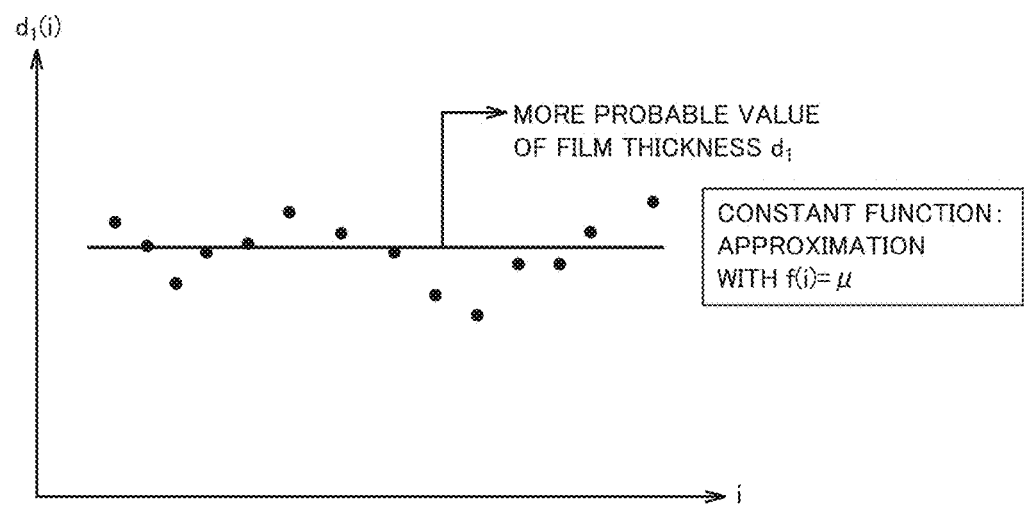
FIG. 27 is a diagram for illustrating a method of determining a more probable value of a film thickness in the refractive index measurement method (No. 2) based on information in a position direction according to the present embodiment.

FIG. 27 is a diagram for illustrating a method of determining a more probable value of film thickness $d_1$ in the refractive index measurement method (No. 2) based on information in the position direction according to the present embodiment. Though film thicknesses $d_1$ as many as wavelength-direction pixel numbers i can be calculated, film thicknesses $d_1$ calculated for wavelength-direction pixel numbers i should be equal in value to one another. As shown in FIG. 27, film thickness trend curve $d_1(i)$ at the time of variation in wavelength-direction pixel number i is approximated to a constant function $f(i)=\mu$ ($\mu$ being a constant value). Constant $\mu$ is then determined such that sum of squared residuals S between $d_1(i)$ and $f(i)$ takes a relative minimum value (a minimum value). Constant $\mu$ thus determined represents a more probable film thickness $d_1$.

More probable film thickness $d_1=\mu$ is given to a term representing a theoretical value of a transmittance in the formula (25), and sum of squared residuals Q between the theoretical value of the transmittance and an actually measured value of the transmittance is defined as in a formula (26) below.

$$Q(i, \mu, n_i(i)) = \frac{B_y}{C_y} \sum_{j=1}^{C_y/B_y} \{T_{theo}(i, j, \mu, n_1(i)) - T_{meas}(i, j)\}^2 \quad (26)$$

By satisfying a condition that sum of squared residuals Q defined in the formula (26) above is minimized, that is, a condition of $\partial Q/\partial n_1(i)=0$ is satisfied, refractive index $n_1(i)$ at wavelength-direction pixel number i of interest and corresponding film thickness $d_1$ can be determined.

Since film thickness $d_1$ has a constant value without depending on wavelength-direction pixel number i and position-direction pixel number j as described above, refractive index $n_1(i)$ calculated for one wavelength-direction pixel number i and corresponding film thickness $d_1$ may be output as final values when wavelength-dependency of refractive index $n_1$ is not taken into consideration (that is, when refractive index $n_1$ has a constant value).

In order to further enhance accuracy in measurement, a set of refractive index $n_1$ and film thickness $d_1$ may be determined for all wavelength-direction pixel numbers i. In this case, a result of statistical processing such as averaging of values of sets of refractive index $n_1$ and film thickness $d_1$ may finally be output.

As will be described in the refractive index measurement method (No. 3) based on the information in the position direction which will be described later, when wavelength-dependency of refractive index $n_1$ is taken into consideration, a plurality of wavelength-direction pixel numbers i should be considered.

Though the formula (26) above is written to use all of position-direction pixel numbers j in calculation of sum of squared residuals Q, all of them do not necessarily have to be used, and a prescribed number of pixel rows may be used in accordance with required accuracy. In this case, measurement points at which sample S is arranged should also be arranged at intervals greater than a resolution in the film thickness measurement method.

Since the processing procedure in the refractive index measurement method (No. 1) based on the information in the position direction is the same as the processing procedure in the refractive index measurement method (No. 1) based on the information in the wavelength direction shown in FIG. 24, detailed description will not be repeated.

Thus, in the present measurement method, film thicknesses of a sample are calculated for a plurality of wavelengths in a distribution of actually measured values based on an error between a distribution of theoretical values and a distribution of actually measured values, and a more probable film thickness is determined based on the calculated film thicknesses.

(f8: Refractive Index Measurement Method (No. 3) Based on Information in Position Direction)

In the description of the refractive index measurement methods (Nos. 1 and 2) based on information in the position direction described above, an example in which a condition of refractive index $n_1(\lambda)=n_1$ (constant value) is satisfied is assumed. In actual, however, refractive index $n_1(\lambda)$ is wavelength-dependent. In this case, refractive index $n_1(\lambda)$ is defined with a high-order formula and each coefficient in the high-order formula is to be fitted, so that refractive index $n_1(\lambda)$ in consideration of wavelength-dependency can be determined.

By way of example, the Cauchy dispersion formula as shown in the formula (18) above may be used. In this case, coefficients (E, F, G) in terms in the formula (18) can be determined by calculating refractive index $n_1(i)$ at least three points at wavelength-direction pixel number i.

In using the Cauchy dispersion formula, a plurality of data rows in the position direction at each wavelength-direction pixel number i can also collectively be handled. Namely, film thickness $d_1$ and the coefficients (E, F, G) for a plurality of different wavelength-direction pixel numbers i can be handled as common parameters without depending on wavelength-direction pixel number i, and the coefficients (E, F, G) can be determined such that sum of squared residuals Q including also the sum for the plurality of wavelength-direction pixel numbers i in addition to position-direction pixel number j is minimized when these four parameters are varied.

More specifically, a set of film thickness $d_1$ and the coefficients (E, F, G) which satisfies a condition of $\partial Q/\partial d_1 = \partial Q/\partial E = \partial Q/\partial F = \partial Q/\partial G = 0$ may be found. The Gauss-Newton method, the steepest descent method, and the Levenberg-Marquardt method can be used for an algorithm in this case.

In yet another method, wavelength-dependency $n_1(\lambda)$ of the refractive index can also be determined by applying the least squares method to the formula (26) above, calculating refractive index $n_1(i)$ for each wavelength-direction pixel number i, and thereafter aggregating refractive index $n_1(i)$ (i=1, 2, 3, . . . , $C_x/B_x$) for each calculated wavelength-direction pixel number i. In this method, it is not necessary to particularly designate a form of a function (a model formula) of wavelength-dependency of the refractive index.

In the procedure as above, refractive index $n_1(\lambda)$ in consideration of wavelength-dependency can be found.

Thus, the present measurement method is set such that a refractive index of a sample used for calculation of a distribution of theoretical values is calculated in accordance with a prescribed wavelength dispersion formula. Then, each coefficient defining the prescribed wavelength dispersion formula and a film thickness are fitted to make smaller, errors between the distribution of the theoretical values and the distribution of the actually measured values for a plurality of wavelengths in the distribution of the actually measured values.

G. Application Examples

Application examples of the optical measurement apparatus according to the present embodiment will now be described.

For example, by being arranged in a film manufacturing line, the optical measurement apparatus according to the present embodiment can conduct in-line measurement of a film thickness. The optical measurement apparatus according to the present embodiment can output an in-plane film thickness distribution (that is, a two-dimensional film thickness distribution) of a sample. For example, a defective portion which may be produced in the film manufacturing line can also be specified based on variation in film thickness trend in a direction of transportation, that is, a machine direction (MD), of the sample.

More specifically, for example, the film manufacturing line includes a plurality of transportation rollers and any transportation roller contains a defective portion such as formation of a projecting portion in the film or introduction of a foreign matter into a surface of the roller. In this case, it is expected that a film thickness is varied with a period dependent on a radius (or a length of a circumference) of the transportation roller or a length of a film wound around the transportation roller. A defective portion in the film manufacturing line can be specified based on periodicity of variation produced in such a film thickness trend in the MD direction (variation in film thickness, production of streaks or unevenness, or production of local unevenness).

Inspection for a defect can thus be conducted by making use of periodicity of a film thickness trend output by the optical measurement apparatus according to the present embodiment.

The optical measurement apparatus according to the present embodiment can be used for any application without being limited to the applications as described above.

For example, a semiconductor, a function film, plastics, and various filters are subjected to in-line measurement of a film thickness.

H. Other Embodiments (h1: Determination of Angle of View and Position of Center Based on Actually Measured Film Thickness Value)

The description above is on the premise that angle of view $\phi(=A \tan(b/2f))$ of measurement optical system 10 is theoretically determined by length b of imaging device 160 and focal length f of object lens 12 based on catalogue specifications.

Depending on a type of object lens 12 to actually be used, however, an effective focal length f may slightly deviate from a catalogue value of focal length f due to distortion of the lens or variation in focusing. It is also expected that it is slightly difficult to match a position of the center of a pixel ($j=C_y/2B_y$) and the center of imaging by imaging portion 16 with each other in optical adjustment.

In such a case, the effective value of the angle of view and the position of the center may be determined based on an actually measured value of the film thickness. For example, a transmittance spectrum or a reflectance spectrum in the wavelength direction when position-direction pixel number j (that is, angle of incidence $\theta_0$) is different for the same sample S is measured. Then, the film thickness is calculated in accordance with the processing procedure (No. 1) in the film thickness measurement method described above without correcting angle of incidence $\theta_0$ for the measured transmittance spectrum or reflectance spectrum. Through such a procedure, a film thickness trend representing variation in film thickness corresponding to each measurement point can be obtained.

By fitting the obtained film thickness trend with a function such as $y=\cos A(x-x0)$ after standardizing a value of the film thickness at the position of the center of a pixel to 1, an effective angle of view $\phi'(=A \tan(b/2f))$ and a position of the center $x_0$ can be calculated based on the actually measured value of the film thickness.

(h2: Parallel Arrangement of a Plurality of Optical Measurement Apparatuses)

When the optical measurement apparatus according to the present embodiment is arranged in a film manufacturing line, a plurality of optical measurement apparatuses according to the present embodiment are arranged in parallel in accordance with a width of the line for the film. In such a case, a portion overlapping with a range of measurement by another adjacently arranged measurement optical system 10 may be created around an end portion of the range of measurement by measurement optical system 10. Namely, it is expected that the same point in sample S is included in a plurality of ranges of measurement by measurement optical system 10. In such a case, results of measurement for the same point in sample S output from the optical measurement apparatuses may be different from each other. Since such inconsistency is not preferred in management of the line, results of measurement may be matched by adopting a modification method as below.

In the optical measurement apparatus according to the present embodiment, influence by an angle of incidence of measurement interference light can be eliminated. Therefore, a film thickness calculated for the same point in a sample is constant regardless of the angle of incidence. For example, a film thickness of a small piece (for example, of a 1-mm square) of the same sample S may be measured with the optical measurement apparatuses, and offset modification and/or a coefficient may be set for the optical measurement apparatuses such that measured film thicknesses (for example, measurement values at measurement points at which the angle of incidence is zero) are consistent.

I. Advantages

As described above, according to the present embodiment, an in-plane film thickness distribution of various samples can be measured faster and more accurately. According to the present embodiment, optical characteristics of a sample such as a refractive index can be measured without using a dedicated measurement apparatus.

Though embodiments of the present invention have been described, it should be understood that the embodiment disclosed herein is illustrative and non-restrictive in every respect. The scope of the present invention is defined by the terms of the claims and is intended to include any modifications within the scope and meaning equivalent to the terms of the claims.

What is claimed is:

1. An optical measurement apparatus comprising:
   an irradiation optical system configured to linearly irradiate a measurement target with measurement light having a certain wavelength range;
   a measurement optical system which receives linear measurement interference light which is transmitted light or reflected light originating from the measurement target as a result of irradiation with the measurement light; and
   a processing device, wherein
   the measurement optical system comprises
      a diffraction grating which expands the measurement interference light in a wavelength direction orthogonal to a longitudinal direction of the measurement interference light, and
      an imaging portion which outputs a two-dimensional image by receiving the measurement interference light expanded in the wavelength direction by the diffraction grating, and
   the processing device comprises
      a first calculation module that calculates a modification factor depending on an angle of incidence on the measurement optical system from each measurement point in association with a region in the two-dimensional image corresponding to each measurement point in the measurement target irradiated with the measurement light, and
      a second calculation module that calculates optical characteristics of the measurement target by applying a corresponding modification factor to each pixel value included in the two-dimensional image.

2. The optical measurement apparatus according to claim 1, wherein
   the modification factor includes a wave number representing a parameter including a wavelength of the measurement light and a refractive index of the measurement target, and
   the wave number is calculated in consideration of magnitude of a corresponding angle of incidence, for each pixel position in the two-dimensional image.

3. The optical measurement apparatus according to claim 2, wherein
   the second calculation module is configured to
      subject a row of values resulting from conversion in accordance with a relational expression for linearizing the pixel value in the two-dimensional image corresponding to a measurement point of interest with respect to a phase factor, to Fourier transform with respect to a row of corresponding wave numbers,
      determine a film thickness at the measurement point of interest based on a peak position which appears in a power spectrum obtained through the Fourier transform, and
      aggregate film thicknesses determined for a plurality of the measurement points and outputting a resultant aggregate as a film thickness distribution.

4. The optical measurement apparatus according to claim 2, wherein
   the wave number is calculated in consideration of wavelength-dependency of a refractive index of the measurement target.

5. The optical measurement apparatus according to claim 1, wherein
   the modification factor includes a value representing magnitude of an angle of incidence corresponding to each measurement point, and
   the second calculation module is configured to
      adopt a film thickness at each measurement point as a fluctuating parameter and calculate a theoretical value of each pixel corresponding to the two-dimensional image based on a refractive index of the measurement target, a value representing magnitude of the angle of incidence corresponding to each measurement point, and correspondence between each measurement point and a pixel position in the two-dimensional image, and
      determine a film thickness at each measurement point by adjusting the fluctuating parameter such that a similarity between the calculated theoretical value of each pixel and each pixel value of the two-dimensional image is higher.

6. An optical measurement method comprising:

linearly irradiating a measurement target with measurement light having a certain wavelength range and receiving linear measurement interference light which is transmitted light or reflected light originating from the measurement target as a result of irradiation with the measurement light;

expanding the measurement interference light in a wavelength direction orthogonal to a longitudinal direction of the measurement interference light and outputting a two-dimensional image by receiving the measurement interference light expanded in the wavelength direction;

calculating a modification factor depending on an angle of incidence from each measurement point in association with a region in the two-dimensional image corresponding to each measurement point in the measurement target irradiated with the measurement light; and calculating optical characteristics of the measurement target by applying a corresponding modification factor to each pixel value included in the two-dimensional image.

7. The optical measurement method according to claim 6, wherein the modification factor includes a wave number representing a parameter including a wavelength of the measurement light and a refractive index of the measurement target, and the wave number is calculated in consideration of magnitude of a corresponding angle of incidence, for each pixel position in the two-dimensional image.

8. The optical measurement method according to claim 7, wherein the calculating optical characteristics includes subjecting a row of values resulting from conversion in accordance with a relational expression for linearizing the pixel value of the two-dimensional image corresponding to a measurement point of interest with respect to a phase factor, to Fourier transform with respect to a row of corresponding wave numbers, determining a film thickness at the measurement point of interest based on a peak position which appears in a power spectrum obtained through the Fourier transform, and aggregating film thicknesses determined for a plurality of the measurement points and outputting a resultant aggregate as a film thickness distribution.

9. The optical measurement method according to claim 7, wherein the wave number is calculated in consideration of wavelength-dependency of a refractive index of the measurement target.

10. The optical measurement method according to claim 6, wherein the modification factor includes a value representing magnitude of an angle of incidence corresponding to each measurement point, and the calculating optical characteristics includes adopting a film thickness at each measurement point as a fluctuating parameter and calculating a theoretical value of each pixel corresponding to the two-dimensional image based on a refractive index of the measurement target, a value representing magnitude of the angle of incidence corresponding to each measurement point, and correspondence between each measurement point and a pixel position in the two-dimensional image, and determining a film thickness at each measurement point by adjusting the fluctuating parameter such that a similarity between the calculated theoretical value of each pixel and each pixel value of the two-dimensional image is higher.

* * * * *